(12) United States Patent
Reda et al.

(10) Patent No.: US 9,540,683 B2
(45) Date of Patent: Jan. 10, 2017

(54) BIOSENSOR ARRAY FORMED BY JUNCTIONS OF FUNCTIONALIZED ELECTRODES

(75) Inventors: Torsten Reda, Vienna (AT); Igor Holländer, Vienna (AT); Alexander Seitz, Vienna (AT)

(73) Assignee: Lexogen GmbH, Vienna (AT)

( * ) Notice: Subject to any disclaimer, the term of this patent is extended or adjusted under 35 U.S.C. 154(b) by 644 days.

(21) Appl. No.: 14/001,929

(22) PCT Filed: Feb. 27, 2012

(86) PCT No.: PCT/AT2012/000043
§ 371 (c)(1),
(2), (4) Date: Sep. 27, 2013

(87) PCT Pub. No.: WO2012/116386
PCT Pub. Date: Sep. 7, 2012

(65) Prior Publication Data
US 2014/0018262 A1    Jan. 16, 2014

(30) Foreign Application Priority Data
Feb. 28, 2011 (EP) .................................. 11450029

(51) Int. Cl.
*C12Q 1/68* (2006.01)
*G01N 27/327* (2006.01)
(Continued)

(52) U.S. Cl.
CPC ......... *C12Q 1/6837* (2013.01); *G01N 27/3278* (2013.01); *B82Y 15/00* (2013.01); *G01N 33/5438* (2013.01); *G01N 33/553* (2013.01)

(58) Field of Classification Search
CPC ............ G01N 27/3278; G01N 33/5438; G01N 33/553; B82Y 15/00; C12Q 1/6825
See application file for complete search history.

(56) References Cited

U.S. PATENT DOCUMENTS

2003/0089899 A1* 5/2003 Lieber ................... B82Y 10/00
257/9
2008/0093226 A1* 4/2008 Briman ............... G01N 27/127
205/775
(Continued)

FOREIGN PATENT DOCUMENTS

EP            2088430 A1    8/2009
WO      2010104479 A1    9/2010

OTHER PUBLICATIONS

Chen Xiaojun et al: "Electrical sensor array for polymerase chain reaction-free messenger RNA expression profiling", Analytical Chemistry, American Chemical Society, US, vol. 82, No. 14, Jul. 15, 2010 (Jul. 15, 2010), pp. 5958-5964, XP007918852, ISSN: 0003-2700, DOI: 10.1021/AC1003135 [retrieved on Jun. 25, 2010].

*Primary Examiner* — Sean E Conley
*Assistant Examiner* — Benjamin Whatley
(74) *Attorney, Agent, or Firm* — Laurence A. Greenberg; Werner H. Stemer; Ralph E. Locher

(57) ABSTRACT

We provide a sensor array device for the measurement of mixtures of organic compounds comprising an assembly of sensor half elements which have been functionalized through sensor compounds before the assembly. Each individual sensor of the array contains two sensor compounds which are bound at opposite sensor half elements. The molecular recognition is bi-functional. While the amount of sensor compounds increases linearly, the individual sensors increase with the second power.

19 Claims, 12 Drawing Sheets

(51) Int. Cl.
G01N 33/553 (2006.01)
G01N 33/543 (2006.01)
B82Y 15/00 (2011.01)

(56) References Cited

U.S. PATENT DOCUMENTS

2009/0102450 A1* 4/2009 Da Silva ............ G01N 33/2823
324/72
2009/0188784 A1   7/2009 Lee et al.
2012/0122715 A1* 5/2012 Gao .................... G01N 27/3278
506/9

* cited by examiner

# BIOSENSOR ARRAY FORMED BY JUNCTIONS OF FUNCTIONALIZED ELECTRODES We provide a sensor array device for the measurement of mixtures of organic compounds comprising an assembly of sensor half elements which have been functionalized through sensor compounds before the assembly. Each individual sensor of the array contains two sensor compounds which are bound at opposite sensor half elements. The molecular recognition is bi-functional. While the amount of sensor compounds increases linearly, the individual sensors increase with the second power.

FIELD OF INVENTION

The invention relates to a sensor array as disclosed in claim 1. Embodiments of the invention relate to the field of biosensor arrays for the detection and characterization of mixtures of different organic compounds, in particular RNA's, DNA's or proteins. Beside their use in the biological, pharmaceutical and medical research such kind of sensor arrays can also be applied in diagnostics. One example is the characterization of gene expression patterns, transcriptomes. Here, the kind of transcripts and their abundance are determined with high precision in order to see relevant difference between cells and tissues of particular origin. Other examples are the detection of microbial contaminations through the measurement of RNA or DNA signatures in samples, the test of antibody titer levels, etc.

According to the current state of the art, determining and quantifying many individual organic compounds in complex mixtures is principally possible but very labor and cost intensive. Not only are the samples often limited in size and therefore precious, also the required analytical chemicals are expensive. The aim is to carry out many similar reactions in parallel. It means that such analysis is multiplexed in smallest possible volumes. The separation of different reactions in volume phase is limited by the number of available and distinguishable labels. Therefore, surface bound reactions with spatial resolution are important for identifying many different molecules isochronal in small quantities. Examples are so called biochips which generate, transduce and amplify signals.

Particular valuable are individual sensor compounds, e.g. hybridization probes, primers or antibodies, to specifically detect different organic compounds in complex mixtures like DNA or proteins through molecular recognition of oligonucleotides and antibodies.

The design of sensor compounds follows the principle to be highly specific for one target. It implies that the recognition of many targets requires at least as many different sensor compounds assorted in sensor compound libraries. This applies to hybridization probes, primer designs and antibodies likewise.

Sought after are designs and their technological realizations of efficient biosensor arrays which minimize the effort and requirement for extensive sensor compound libraries.

BACKGROUND OF THE INVENTION

Detection of Biomolecules

The detection of organic molecules in extremely tiny amounts is challenging. Optical and electromagnetic properties describe the ability of the compound under investigation to absorb and alter a steady or alternating energy flux. Each compound does absorb light energy, absorbance. Some dissipate this energy as heat while others emit it partly in form of light of lower frequency, fluorescence. Light can be applied and collected by scanners with lateral resolutions down to micrometer range.

Molecular electromagnetic and electronic properties are in the limelight for sensor applications. To detect magnetic properties of electron or nucleus spins substantial amounts of material are needed. Electrochemical properties, reduction potentials, can be utilized to identify redox-active centers in hosts, but only a limited number of compounds carry such centers. Measurements of molecular conductivities are difficult through the challenges of establishing proper working connections.

Therefore, different methods have been developed to increase the conductivity of both, electrode-molecule connections and molecules themselves, e.g. through the metallization of polynucleic acids by adsorption and subsequent reduction of silver ions [Braun, 1998]. The utilization of conductivities as measurand in sensor array networks is cumbersome because each measurement cell needs to be contacted by two electrodes. Such setups require a potentially high number of electrodes and contacts respectively. In networks of interconnecting electrodes, where at each intersection or junction the conductivity can change due to analyte interaction, it is not possible to distinguish between the electrical current passage through one particular junction and alternative pathways thru other junctions. It is not possible to achieve matrix field or lateral resolution of m×n measurement cells with m×n electrodes when measuring resistances.

Without the need of a net direct current, DC, it is possible to probe a sample volume through a changing electric field, e.g. caused by an alternating current, AC. Electrical readouts provide in general the potential to use capacitive electric field, inductive magnetic field, resistive sensing and combinations thereof. Capacitive biosensors are disclosed in U.S. Pat. No. 5,532,128, US 2004/0110277 or WO 2009/003208. The general principle is the change of the dielectric hence capacitance in the sensor element through the presence of target molecules.

Capacitive or impedimetric biosensors are based on impedance spectroscopy, IS, electrochemical impedance spectroscopy, EIS, or charge based capacitance measurements, CBCM. An in-depth explanation of the mathematical derivation of the physico-chemical and electrochemical parameters concerning IS has been written by A. Lasia [Lasia, 1999]. An overview by Lisdat and Schäfer [Lisdat, 2008] focuses on the use of EIS in biosensing.

EIS is a complex method which measures simultaneously all elements of a circuitry including charge transfer processes at the interfaces and conductivity of the electrolyte. Impedimetric biosensors were tested for immunosensing, enzyme studies, cell based assays and nucleic acid determination. Focusing at the interfacial reactions, experiments with nucleic acids have shown that EIS is capable to discriminate between single stranded ssDNA, and double stranded dsDNA [Hasoň, 2002; Strasák, 2002], to monitor hybridization [Drummond, 2003; Kelley, 1999; Fojta, 2003; Hashimoto, 1994; Pänke, 2007], melting of hybrids [Scuor, 2007] and intercalation [Xu, 2006]. Furthermore, EIS could detect single base pair mismatches [Cho, 2006; Pänke, 2008, Vermeeren, 2007], differentiate between DNA structures such as B- or M-DNA, probe DNA-analyte interactions, e.g. DNA with the cross-linking agent cis-platin [Yan, 2001] or with specific DNA binding proteins [Li, 2004].

Besides the monitoring of interfacial reactions it is also of great interest to detect materials like nucleic acids in the volume phase. The dielectric behaviour of DNA has been investigated over a wide frequency range from ultra low to microwave frequencies of 70 GHz. In contrast to water with a dielectric constant, $\in_r$, between 88 and 55.3 at 0 and 100° C., respectively, does a diluted solution of DNA display larger $\in_r$-values with approximately 120 at 20° and 100 kHz for 1% DNA solution in water [Takashima, 1984]. However, many pure organic polymers have smaller $\in_r$-value ranging typically between 2 and 10 at 20° C. Some polymers with widely extended electron orbitals can show $\in_r$-values as large as $10^5$ as it has been measured for 2-chloroanthraquinone/tetra-chlorophthalic anhydride at 1 kHz [Pohl, 1985].

Because signal differences are usually small, increasing the signal to noise ratio is important. The classic approach uses large working electrodes which provide the significant capacitance in the system. Dendrimers [Li, 2007] and polymer structures are used to further maximize the surface areas [Maupas, 1997]. Peroxidase coupled reactions have been exploited as transducer [Ma, 2006] as much as nanoparticles [Peng, 2006; Li, 2005; Cai, 2003] or liposomes [Patolsky, 2003; Patolsky, 2001].

Alternatively, signal intensity can be enhanced through the alignment of the electrodes [Van Gerwen, 1998; Laureyn, 2000; Gheorghe, 2003; Dharuman, 2005] where the strength of the electric fields can be maximized by keeping electrodes in very close proximity [Montelius, 1995]. The signal increases linearly with length which can be realized through the winding structure of interdigitated electrodes, IDE. So far, distances depend on the manufacturing process and range from 10 to 1 μm [Brewood, 2008] with electrode widths as small as 500 to 200 nm [Van Gerwen, 1998]. Such IDE's have been used for investigating DNA hybridizations [Gheorghe, 2003; Dharuman, 2005; Van Gerwen, 1998; Hang, 2004; Berdat, 2006] and for the measurement of DNA concentrations. 200 pF responses have been obtained for 1 pM 2.961 bp phagemid pBluescript DNA solutions, which corresponds to approximately 1,1 DNA molecules per μm$^3$ only [Henning, 2008]. The extrapolation to smaller electrode sizes hence smaller volumes and signals indicate the possibility to detect very few DNA molecules with signal differences in the order of 10 fF.

Further advancements can be envisaged through the use of nanogap-impedance sensors which promise high sensitivities due to their large surface-to-volume ratio and because electrode polarization effects become negligible. For minimizing shielding through buffer-ions, a microwave frequency, 1.28 GHz, has been used to sense antibody-thrombin binding in a 75 nm gap of an electrode area of 96 μm$^2$ [Schlecht, 2006]. Nanocapacitors based on pore structures and gaps are discussed and modeled with the aim to use the method for polynucleotide sequencing [Sigalov, 2008; Lu, 2008]. These publications highlight the influence of the electric double layer, EDL, impedance which generates interfering noise levels at low frequencies kHz range. When the gap sizes become comparable or smaller as the EDL thickness, $d_{dl}$, the nanogap capacitance will become independent of ionic strength, I. So is $d_{dl}$ 960 nm for I of $10^{-7}$ M but only 9.6 nm for $10^{-3}$ M solutions. In addition, the electric field distribution changes with gap size. Smaller gap sizes lead to potential increases in the centre and potential decreases at the electrode surfaces. The electric field becomes more homogeneous [Yi, 2005]. Eventually, for gaps, tubes, wires and other devices in the range of 10 nm and below quantum effects become important for the accurate description of reactions at electrode surfaces. So far, numerous techniques like electron beam lithography [Hwang, 2002], electrodeposition, electromigration [Iqbal, 2005] or other electrochemical methods, composite layer build-up combined with etching [Steinmüller-Nethyl, 2009] and fracture techniques [Reed, 1997; Reichert, 2002] have been employed to separate two electrodes by a tiny nanometer sized gap.

Segregation of Biomolecules and Sensor Arrays

In contrast to sequential measurements the quasi instantaneous measurement of molecules in complex mixtures requires segregation of the sample. This segregation reduces the degree of entropy in the system and facilitates efficient parallel measurements. Different classes of molecules are segregated into separated locations, e.g. spots. The predetermined position characterizes the class of molecules whereas the signal intensity at this position determines the amount which translates into concentrations of the compound in the sample. Microarrays are typical examples where single probes, sensor compounds or sequences, have been immobilized at a solid surface in specified regions [Southern, 1997]. For example, after a complex mixture of different sequences has been applied to a DNA microarray, only molecules with complementary sequences will hybridize to predetermined spots and generate a certain signal pattern. Disadvantages of such single probe designs are that many different classes of molecules might contain the same sequence, e.g. in the case of cognate genes or their splice variants, and each molecule might contain sequences which match to numerous different probes. The data analysis becomes very challenging and remains ambiguous.

Longer sequences also allow using of dual probes. Here, two single probes act like molecular brackets which are specific towards two distinct sites. The design allows more flexibility as one single bracket and can be chosen to target conserved regions, e.g. certain core exons of genes, while the other bracket is reaching to a region of flexibility, e.g. to exons which are characteristic for certain splice variants. Signal amplifications are possible, when the probes are designed as primers for polymerase chain reactions, PCR, which can be carried out in volume phase and at solid supported phase like sensor surfaces. Here, two primers are applied to a single sensor surface either sequentially or as a mixture to form a rather ideal 2D mixture of molecules at such surface. If a target molecule binds to such surface it can initiate an origin or seed for amplification and in succession a surface supported PCR reaction. Here, one difficulty is that different sites of the target molecule react with the very same surface. The target molecule and its copy, the amplicon, firstly, do not stick to the surface to enable the efficient enzyme catalyzed polymerization at the surface, but secondly, "bends" towards this surface in order to react with the second probe. Such amplification has been named "bridge amplification" because the molecules from a bridge from one probe to another probe [Boles, 2002]. The bridges develop along a single 2D surface where seeds can only grow geometrically to form small product islands which extend predominantly along their edges only. The resulting PCR efficiency, E, can start of high, with E being close to one. E will drop after several cycles [Mercier, 2003; Adessi, 2000].

The combination of impedimetric sensors and dual probes makes it visible to employ two differently functionalized electrodes in close proximity. The individual modification of electrodes is already difficult and becomes extremely challenging in nanometer range. The making and addressing or functionalizing of such electrode structures would require the use of e.g. very expensive electron-beam lithography techniques. In WO 2009/003208 Steinmüller-Nethyl et al. have proposed to use different materials for each electrode while the electrodes are separated trough an insulating layer with a thickness of only several nm. Here, different electrode materials enable the successive and selective binding of the molecular probes. However, the number of electrically conducting but different materials together with a specific and effective binding chemistry is limited and not practical for large arrays. The geometrical alignment in a set of crossing rows and columns is not possible. Importance of the publication is the description of the principle where analyte molecules with two selective binding sites bridge two electrodes containing one corresponding binding site respectively, and where subsequently the bridging molecules are detected not through DC but AC analytical methods. In US 2002/0022223 and US 2006/0019273 Connolly et al. have already described electrode couples where each electrode has to be modified with one type oligonucleotides. Analytes which contain corresponding sequences to both electrodes can hybridize, bridge and electrically connect electrodes. Such reactions can be recorded through DC signal changes. However, the selective modification of pre-manufactured electrode assemblies is very challenging, time consuming and expensive. Furthermore, all DC sensors are aligned in parallel. Because the number of electrodes and in particular their contacts increases linearly with the number of sensor pads such devices approach fast their technical limitations regarding integration density.

An identical approach has been followed in WO 2010/104479 using electrode arrays where the sensor action occurs at electrode crossings between electrode edges. The electrodes are just nanometers apart from each other and separated by an insulating layer. Here, the problem of selectively immobilizing capture probes on one of two corresponding electrodes across a separating step in the order of few nanometers, experimentally realized were 5-20 nm, has been recognized to be impossible by means of robotic spotters. The chosen method involves the binding of thiol-functionalized probes to all gold-electrodes, the selective removal by electrochemical stripping and repeated binding of thiol-functionalized probes to the second gold-electrode and so forth. Each functionalizing requires 2 hours for the binding step alone plus the time which is required for additional stripping and washing steps. Not only the production method is unsuitable to build complex sensor arrays, also the method of conductance measurements is preventing to utilize truly combinatorial approaches of the capture probes as described above. WO 2010/104479 presents a sensor array as the combination of different capture probes which are immobilized at parallel electrodes, e.g. rows, and bind to specific sequence in mRNA molecules, with explicitly one annealing probe at all columns. The chosen 21 nucleotide long capture probes are so long to serve the purpose to be specific for one particular mRNA only. This markedly high specificity has been chosen to detect per row only one target mRNA each. Therefore, the opposite annealing probe contains one single universal polyT-sequence which binds to all polyA-ends of the mRNA in the sample. Such array presents the complexity of just m×1. The additional columns only increase the effective sensor area by multiplying the number of identical sensors. The presented system is consistent with the chosen measurement method which only allows to distinguishing signals which arise from one entire line, here for example from one entire row.

The smallest dielectric gap concepts are not only aiming to quantify but also to sequence nucleic acids [Lee, 2005]. The proposed structures measure only a few nanometers. Those gaps can be described as tiny plate capacitors which record nucleotide specific changes of the dielectric as polynucleic acids pass through such gaps. The dielectrics properties of the nucleotides are one contribution, the other are the effects that the dielectric constant of bound and semi-bound water is significantly smaller than the one of free water. The estimates for the reading speed are based on using MHz frequencies and would therefore range in the order of 1 Mio reads per second.

The integration of individual sensors is essential for detecting different compounds simultaneously in one sample. Early attempts dealt with difficult sensor arrays where each field had been connected though a separate pair of electrodes [Albers, 1999]. In WO 2004/001405 Frey et al. describe a design and operation of a biosensor array where multiple biosensor fields are arranged matrix-like on a substrate. Each field is addressed through one actuator and one detector line, and each line is able to address several fields. At the time of probing one particular field all other lines are set to a fixed potential e.g. floating ground, unless fields were grouped before. Although it is not explicitly stated, the description contains interdigitated electrodes IDE in each sensor field. The design solved the problem of addressing many fields with minimal connections, however the degree of integration is limited and the manufacturing technologies of said structures are expensive. The issue of modifying said structures differently in each sensor field remains challenging when it comes to tiny dimensions. Along the same line are proposals made by Maeda [2004], Maracas G. [2000] and Li [Li C., 2005], who are separating individual sensor test cells. A similar approach has been followed in CN 101046458 by Liu [2007] who describes an array of crossing electrodes on a substrate which have been insulated from their neighbours through separated micro flow ponds.

Further, from the state of the art the publications WO 2010/1204479 and EP 2088430 are known. WO 2010/1204479 is directed to a sensor for detecting a nucleic acid molecule comprising an electrode arrangement with two electrodes and nucleic acid probes immobilized at the surface of the electrodes. The present invention also refers to a kit and a method of using the sensor or a sensor array. The present invention is further directed to a process of manufacturing a sensor and sensor array.

EP 2088430 provides a bio-sensor including nanochannel-integrated 3-dimensional metallic nanowire gap electrodes, a manufacturing method thereof, and a bio-disk system comprising the bio-sensor. The bio-sensor includes an upper substrate block having a plurality of metallic nanowires formed on a lower surface thereof and including an injection port through which a biomaterial-containing sample is injected, a lower substrate block having a plurality of metallic nanowires formed on an upper surface thereof, and a supporting unit supporting the upper and lower substrate blocks so that the upper and lower substrate blocks can be disposed spaced apart at a predetermined distance to form a nanochannel, wherein the metallic nanowires formed on the upper and lower substrate blocks are combined to form three-dimensional metallic nanowire gap electrodes.

SUMMARY OF THE INVENTION

It is the main objective of the present invention to describe a novel design of biosensor arrays and its technological realization for the fast and quasi-simultaneous analysis of complex mixtures of biomolecules which differ predominantly in their alternating sequence of side chains. These are in particular polynucleic acids like RNA and subsequent cDNA molecules of highly versatile transcriptome origin, but can also be DNA, polypeptides or any derivatives of such.

The invention provides the solution and describes the making, processing and use of highly integrated gap junction sensor arrays. The processing of the described miniaturized and scalable device can be automated to investigate precious small sample sizes in a cost effective way.

A preferred aspect of the present invention utilizes smaller, multi-target sensor compounds. Those sensor compounds are used to functionalize sensor half elements first before the assembly of the sensor half elements creates the sensor array with as many individual sensors as junctions between the sensor half elements. Each individual sensor is characterized through the combination of two sensor compounds. The invention describes the implementation of the combinatorial sensor design principle where m+n sensor half elements are assembled to build one sensor array of n×m individual sensors. Such sensor arrays require much smaller numbers of different sensor compounds as conventional counterparts.

A further preferred aspect of the present invention provides a sensor array that can be evaluated internally via the cores of the sensor half elements, e.g. by impedance measurements, or scanned from extern. The measurand are signal changes in each individual sensor. In particular, impedimetric measurements provide a sensitive method for the label-free detection of analyte concentrations by electrical means. Here, each individual sensor is accessed through the conductive cores of the sensor half elements. Small gap sizes between the electrodes are important for the increase of signal-noise ratio in such impedance or capacitive measurements. At tiny submicrometer dimensions the challenges lie in, firstly, aligning electrodes as narrowly as possible but preventing short circuits, secondly, leaving enough space for analyte to enter the gap between the electrodes and thirdly, modifying individual junctions with different molecular probes.

The invention solves the objective with a sensor array according to patent claim 1. The invention relates to a sensor array a) comprising a plurality of sensor half elements for the measurement of the concentration and the identification of a plurality of organic target compounds under investigation or related copies thereof within a mixture of organic compounds, b) further comprising a plurality of different sensor compounds wherein each sensor half element contains and/or carries one of said sensor compounds, the sensor compounds binding to a specific binding site of said target compounds respectively, c) wherein each of said sensor compounds is assigned to at least one of the sensor half elements, d) wherein each sensor half element intersects or traverses at least one of the other sensor half elements in a separate junction area, e) wherein the sensor compounds of two intersecting or traversing sensor half elements are spaced and/or converge and/or touch each other, f) wherein in each junction area an individual sensor is formed with a determined combination of two sensor compounds each sensor compound being located at one of the intersecting or traversing sensor half elements and g) wherein the sensor array comprises at least two junction areas with different combinations of sensor compounds.

Another preferred aspect of the invention solves the objective with a sensor array according to patent claim 17. This aspect of the invention provides a sensor array a) comprising a plurality of sensor half elements for the measurement of the concentration and the identification of a plurality of organic target compounds under investigation or related copies thereof within a mixture of organic compounds, b) further comprising a plurality of different sensor compounds wherein each sensor half element contains and/or carries one of said sensor compounds, the sensor compounds binding to a specific binding site of said target compounds respectively, c) wherein each of said sensor compounds is assigned to at least one of the sensor half elements, d) wherein each sensor half element intersects or traverses at least one of the other sensor half elements in a separate junction area, e) wherein the sensor compounds of two intersecting or traversing sensor half elements are spaced and/or converge and/or touch each other, f) wherein in each junction area an individual sensor is formed with a determined combination of two sensor compounds each sensor compound being located at one of the intersecting or traversing sensor half elements and g) wherein the sensor array comprises at least two junction areas with different combinations of sensor compounds, h) characterized in that the sensor half elements are aligned in a grid structure, with a plurality of row elements and a plurality of column elements, i) wherein the row elements being formed by a number of sensor half elements and the column elements being formed by the remaining sensor half elements, j) wherein the row elements being aligned and spaced next to each other and the column elements being aligned and spaced next to each other k) wherein each row element intersects at least to, preferably each column element, in at least one junction area, and l) wherein each junction area forms an individual sensor.

Such a sensor array enables the quasi-simultaneous measurement of numerous individual sensors. Because each sensor carries two potentially different sensor compounds, one at each surface, it is possible to provide a sensor with a plurality of unique junctions. With the assembly of m+n sensor half elements up to m×n different classes of molecules can be detected. Such a device can be used to segregate and determine nucleic acids. When nucleic acids react in the gap region of junctions, their electromagnetic and optical behavior, e.g. dielectric constant or fluorescent properties after labeling, will change. Such sensor array can be produced in very small scales because each junction requires just an area of very few square micrometers. The sensor array can be combined with automated procedures, which increases the efficiency of the detection method. The sensor array can operate in a single volume phase where the whole analyte mixture is exposed to, and can interact with all individual sensors of the array.

Furthermore, claim 1 differs from EP 2088430, because EP 2088430 does not disclose a grid structure, EP 2088430 does not even disclose elements that are comparable with row elements or column elements at all. The single elements are not arranged in parallel or grid-like so that there is nothing disclosed that would be comparable to a sensor array. It is therefore only possible to functionalize the sensor disclosed in EP 2088430 with one single substance, while the invention requires at least two substances. Therefore the present invention is novel over EP 2088430.

WO 2010/1204479 describes a sensor device comprising—according to the wording of claims 1.—"a first electrode and . . . second electrode", and claim 6.—"multiple sensors . . . arranged in a sensor array". The main difference between the disclosed sensor device and the present invention is that WO 2010/1204479 does not teach a functional grid structure and further does not disclose a functionally different plurality of row elements. Therefore the present invention is novel over WO 2010/1204479. WO 2010/1204479 is considered to be closest state of the art.

By the arrangement according to the invention using row elements and column elements it is possible to generate a plurality of n×m sensors with different sensor capabilities while only n+m sensor half elements have to be functionalized.

Therefore, it is the main objective of the invention to provide a sensor that is simple to produce, requires a minimal set of functionalizations only, and which is sensitive to a large number of different target compounds in a mixture of organic molecules.

WO 2010/1204479 only discloses the use of one single row element and a plurality of column elements, which is the origin of the sensor array with multiple sensors. The repetition of further row elements with the same functionalization has solely the purpose of increasing the repetition of the same specific signal to further enhance the signal-to-noise ratio of the same specific signal. In order to provide the advantageous effect of the invention and increase the true number of different sensors it is necessary to provide more than one row element and more than one column element. Otherwise the number of sensors approximately equals the number of functionalized elements and no additional effect would be obtained.

Furthermore, the explicit disclosure of WO 2010/1204479 does not allow the fabrication of two-dimensional sensor arrays. The row element shown in black is functionalized with polyT-oligonucleotides homooligomer material that nonspecifically binds to all m RNA target molecules. Only the functionalizing sensor compounds at the column-elements, shown in white, binds specifically to certain target molecules. In the disclosure of WO 2010/1204479 sensor compounds with 21 nucleotides are used, which is highly specific and emphasizes the matter, that the sensor compound shall only be used for one distinct single sensor which targets one specific compound.

The disclosure of WO 2010/1204479 does even dissuade the person skilled in the art from reusing the same sensor compound for different sensors. The first compound, the polyT-oligonucleotide homooligomer annealing probe that is used for the row elements is nonspecific. Multiple uses would not lead to more different specific sensors. The second compound comprising a sequence of 21 nucleotides is extremely specific so that multiple uses are also not possible.

A person skilled in the art is therefore persuaded to use polyT-annealing probes and one highly specific sensor compound, which leads to functionally one dimensional structures, because polyT-annealing probes cannot be replaced by some comparable substance.

It is also not obvious that a different functionalization is performed on both row elements and column elements, WO 2010/1204479 teaches to functionalize only one of these group of elements.

The detection of n×m different substances is exclusively possible, if the sensor compounds are arranged on plurality of row elements and column elements, so that a permutation of different sensors can be obtained.

Based on the disclosure of WO 2010/1204479 using polyT-annealing probes a person skilled in the art would not be able to fabricate a sensor array according to the invention and he would not be able to obtain a number of sensors that is drastically larger than the number of functionalized elements.

A further special aspect of the invention provides a sensor array wherein the sensor half elements are aligned in a grid structure, with a plurality of row elements and a plurality of column elements, the row elements being formed by a number of sensor half elements and the column elements being formed by the remaining sensor half elements, the row elements being aligned and spaced next to each other and the column elements being aligned and spaced next to each other wherein each row element intersects at least one, preferably each, column element in at least one junction area, and wherein each junction area forms a individual sensor, wherein preferably the number of row elements equals the number of column elements.

This sensor array, featuring m row elements and n column elements, enables the detection of m times n different analytes. The sensor-space and therefore the resolution of the sensor array grows quadratically with the number of sensor half elements. For impedimetric sensor arrays, which use the electrical connections via the sensor half elements, only m+n connectors are required to address m×n individual sensors. The number of contacts remains small compared to the number of individual sensors, which is advantageous for the technical realization of electrical contacts and the design of sockets. Each combination of selective sensor compounds detects specifically one group of analytes. With the increase of the number of sensors increases the resolution of the sensor array, which leads to an increased likelihood of detecting individual analytes. The chance to detect rare molecules in complex mixtures will increase with larger sensor arrays. Furthermore, it is possible to combine the sensor array with subsequent analyses methods like mass spectroscopy and next generation sequencing.

As mentioned, an increase of the matrix size increases the performance and the amount of retrievable information. For investigating transcriptomes matrix sizes in the order of several hundred thousands of different fields are required to singularize individual transcripts. The present method enables, for example, to provide one million different individual sensors by means of just 2000 different sensor half elements hence sensor compounds.

Preferably, it is provided that at least one of the sensor half elements or all sensor half elements contain a carrier, the carrier preferably being selected from the group of filament, string, wire, conductor, band or fibre, wherein the carrier supports a layer of the respective sensor compound and/or the carrier comprises the respective sensor compound. This facilitates the stability of the sensor half elements and provides the base for further modifications. The functionalizing with the individual sensor compound converts an interchangeable sensor half element raw component into the ultimate sensor half element.

Advantageously it is provided, that at least one of the sensor half elements or all sensor half elements contain a surface-bound carrier material layer, the material layer containing the sensor compound. This increases the stability and further handling of the sensor half elements.

A further preferred embodiment of the invention is characterized by a common carrier, wherein a plurality of sensor half elements are arranged on a common carrier, or a common carrier comprises said a plurality of sensor half elements or a number of sensor half elements are formed as part of the common carrier, the common carrier preferably having the shape of a plate.

This facilitates the assembly of the sensor half elements to the sensor array because one group of sensor half elements has been already pre-assembled on a supporting carrier.

Another preferred embodiment of the invention is characterized by a first common carrier and a second common carrier, wherein the row elements are located or arranged on the first common carrier or are formed as part of the first common carrier and wherein the column elements are located or arranged on the second common carrier or are formed as part of the second common carrier, the first common carrier and/or second common carrier preferably having the shape of a plate.

This facilitates easier assembly of the sensor half elements to the sensor array because all sensor half elements have already been pre-assembled on two supporting carriers.

Advantageously, it is provided, that the first common carrier and/or the second common carrier are made of material or contain material or support a material layer, the material or the material layer containing the sensor compound of the respective sensor half element in separated areas.

This sensor features sensor half elements that craft directly into or onto the supporting carriers which facilitates again the assembly of the sensor array.

Preferably, it is provided that the respective sensor compound is arranged exclusively in the junction areas, or that the respective sensor compound covers at least a part or especially, the complete surface of the sensor half elements.

This reduces the amount of sensor compound required. In addition, the sensor compound can be restricted to areas which will become part of the prospective sensor junctions or junction areas and only very little quantities of sensor compound will be present outside the sensor junction or junction area. By implication, those areas cannot interfere with the sensing process through scavenging of the analyte.

A further aspect of the invention relates to a sensor array characterized in that the carrier is an electrical conductor or optical conductor or wave guide or are made from such conductors or wave guides, wherein the electrical or optical conductors or the wave or guides are preferably made from metal, glass fibre or conducting polymer.

Material is provided which can transmit electromagnetic or optical signals which leads to the ability to address each junction, hence each individual sensor, via the core of individual carriers of the sensor half elements. Such detection principle circumvents the need for movable mechanical parts and expensive optics as it is the case of conventional scanners.

To improve the quality of impedance measurements conductors are insulated to prevent each junction from short circuit at the point of contact. It is therefore preferably proposed that the carrier contains an electrically insulating layer which partially or entirely surrounds the electrical conductor. For further improvement of quality of impedance measurements it is proposed, that the sensor compound is located and/or immobilized at the insulating layer.

A further preferred aspect of the invention is characterized in that the insulating layer contains a material in which the sensor compound is embedded. The proposed combination of insulating and functionalized surfaces further improves the quality of measurements.

Preferably, it can be provided that the sensor compound is contained in a carrier material layer, preferably in a gel or polymer, which is preferably arranged on the insulating layer and/or coating the insulating layer. The use of porous polymers or gels facilitates the fabrication of a soft matter coating, which enable to easier approach or to assemble surfaces of different sensor half elements to one effective sensor junction or junction area. When two different functionalized soft matter surfaces form one interlaced interfaces then are both sensor compounds present along that interface. The formed structure can be interfused by solvent and analyte.

Advantageously it is provided that at least a portion of the circumference of the cross-section of the sensor half elements is convex, said cross section preferably being approximated circular or elliptic. This enables that during the assembly two sensor half elements can be approached to each other up to the point of hard physical contact. Further advantageously is that next to the contact point widens a space which has molecular dimensions and is accessible from the outside by the analyte. In such junction areas is the analyte capable to react with both surfaces dating from the different sensor half elements.

Preferably, it is provided that the gap of the junction area between the sensor half elements is at least partially cuneiform and/or slit shaped and/or said gap comprises a narrowing region. This improves the quality of the measurement results and ensures that each analyte is detected by two sensor compounds.

Preferably, it is provided that the sensor half elements contain a structured and/or waveliked and/or porous and/or rough surface. This enhances the extent of surface interactions through structuring of the active surfaces because increased surfaces present more sensor compounds per junction and the sensitivity increases accordingly.

Based on the combination with supporting plates is it advantageous to craft the sensor half elements directly onto or into the supporting plate during one technological processing step. According to a preferred aspect of the invention the sensor array can be imported in such manner that that the sensor half elements are arranged on elevations or in cavities of the first common carrier and/or the second common carrier. This simplifies the technological realization of the sensor array. The stability of the assembly increases because aligning and mounting of the sensor half elements is not required.

Preferably, the sensor half elements are aligned in a woven structure to advantageously fix all junctions in their positions with defined neighbours. Contacts between the sensor half elements are inevitable and stable. Furthermore, the sensor half elements entangle each other to some degree which enhances the contact area. Woven structure can be produced as de facto 2D sheet or 3D structure, e.g. as a tube, or become folded afterwards. By this means, the presented sensor arrays can be more easily integrated with microfluidic systems. The difference to standard weaving techniques is that as many warps and wefts as sensor half elements are required.

Alternatively, the sensor half elements are combined in a feltlike or unordered structure, so that each sensor half element forms at least one junction with another sensor half element. Advantages of this kind of assembly of sensor half elements are that it is not necessary to perform a mechanical difficult weaving or otherwise aligning process in micrometer scales where fragile wires and fibers are controlled in their spatial positions. The sensor half elements are easier to connect because all connections can be made before the random assembly process starts.

A preferred aspect of the invention is characterized in that the sensor half elements are straight and contact each other in the respective junction area, the junction area preferably being a punctiform region, or that the sensor half elements are curved and contact each other in the respective junction area, said junction area preferably being a unidimensional line or two dimensional region. The variability in the formation of the contact area between two sensor half elements allows sensitivity tuning. The effective sensor areas can be small circles, rings and more elongated closed paths.

Another preferred aspect of the invention is characterized in that the row elements are aligned in a first plane and the column elements are aligned in a second plane,
wherein the row and column elements are narrowed to each other in the junction areas or touching each other or junction areas converge.

This preferred aspect enables the straight and well defined assembly of sensor half elements which does not require a weaving technology. The array structure is well ordered and can be probed by independent, e.g. optical, scanning technologies when transparent carrier materials are employed. The lateral position of the junction can be linked with the particular pair of sensor compounds.

In order to add stability to the sensor assembly the sensor array can be characterized in that the first common carrier and the second common carrier are planar plates or frames, and that said carriers contacted in a manner that the row elements approach or contact column elements within a junction area, and that the sensor compounds of the sensor half elements approach each other in junction areas.

Preferably, it is provided that within the junction areas the sensor compound molecules of the row sensor elements and the sensor compound molecules of the column sensor elements are spaced at most in a manner that the organic compounds under investigation or related copies are able to bind to the respective sensor compound arranged on the row elements with a first binding site and to the respective sensor compound arranged on the column elements with a second binding site and/or that the respective sensor compounds of the sensor half elements contain oligonucleotides, binding to binding sites of the target compounds or organic polymers or DNA or RNA molecules. The enormous sequence variability and complexity makes polynucleotides ideal targets for the presented sensor arrays which segregate and measure complex mixtures. The sequence specific molecular recognition through complementary pairing enables oligonucleotides to act as potent sensor compounds to detect polynucleotides.

Preferably, the respective sensor compounds of the row elements bind to the start sites of organic polymers or DNA or RNA molecules and that the respective sensor compounds of the column elements bind to the end sites of an organic polymer or DNA or RNA molecules.

This allows the detection from start to end and therefore the measurement of full length molecules.

Advantageously the sensor array further comprises an evaluation unit comprising
a first selection unit with one primary port and a plurality of secondary ports which are individually connected to one sensor half element each,
a second selection unit with one primary port and a plurality of secondary ports which are individually connected to one sensor half element each,
a control unit which controls the selection units to address and/or select a first sensor half element with the first selection unit and a second sensor half element with the second selection unit,
a measurement unit to record electrical, electromagnetic or optical parameters, connected to the primary ports of the primary and secondary selection units,
the measurement unit preferably being an impedance, electromagnetic wave impedance, capacitance, light absorption detection unit
wherein preferably the row elements are individually connected to the secondary ports of the first selection unit and the column elements are individually connected to the secondary ports of the second selection unit.

This simplifies the measurement of a large plurality of sensors by use of linear sensor half elements with conducting carriers, electrodes or optical fibers which allow to addressing each junction directly through the elements of the structure. No scanning devices with movable parts are required which makes the device more cost effective. One particular improvement is the measurement of impedance changes caused by polynucleic acid concentration changes in sensor junctions or junction areas. DNA entering the gap region changes its dielectric from the corresponding value of water with $\in_r$ of 80 at 1 MHz to >90 of a 1% DNA solution [Takashima, 1984]. Under dry conditions lie characteristic $\in_r$ values of pure organic polymers between 6 and 8.

Preferably, the sensor array further comprises
at least one optical radiation source directed towards the junction areas,
at least one optical radiation detecting unit also directed towards the junction areas,
the optical radiation detecting unit measuring radiation absorbed and/or re-emitted by the organic compounds under investigation, which are bond to the sensor compounds in the respective junction area.

This enables the readout of the sensor array through optical scanner systems which have been developed for various other sensor arrays like microarrays. This preferred aspect of the invention can be further improved by the use of transparent carriers.

DETAILED DESCRIPTION OF PREFERRED EMBODIMENTS

Preferred embodiments of the present invention will be described in detail below with reference to the drawings.

First Preferred Embodiment

Woven Network of Conductors—from the Array Assembly to the Measurement

Figure 1:
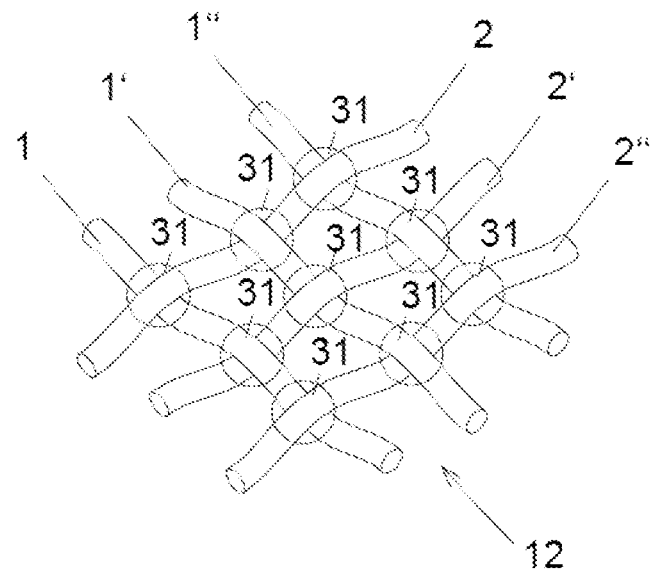
FIG. 1 is an oblique view of a woven network with numerous sensor half elements.

The first preferred embodiment of the invention, which is shown in FIG. 1, describes a sensor array 12 with woven sensor half elements 1, 2, which are grouped as row elements 1 and column elements 2. One group of unidirectional sensor half elements 1, 2 is denoted as row elements 1. The remaining sensor half elements 1, 2 are referred to as column elements 2. Together, the sensor half elements 1, 2 are assembled in a weave-like or woven structure. Accordingly, each row element 1 intersects or crosses or approaches or touches each column element 2 in exactly one junction area 31. The number of junction areas 31 within one sensor array 12 equals to the product of the number of row elements 1 and column elements 2.

Figure 2:
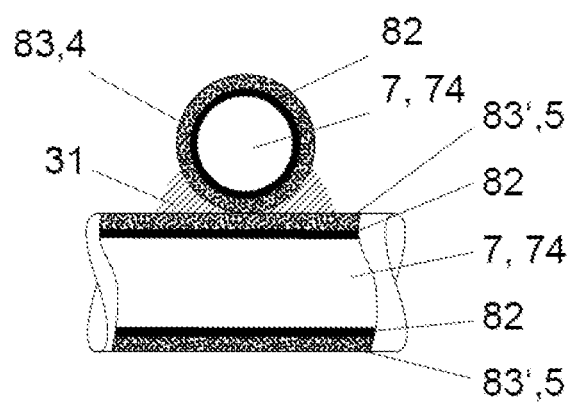
FIG. 2 shows the cross-section view of the junction area between two sensor half-elements.

The present example contains linear sensor half elements 1, 2 as shown in FIG. 2. The carrier 7 is an elongated conductor 74 and has a convex almost circular cross-section. The cross section of the respective sensor half elements 1, 2 does not change along the lateral extension of the sensor half element 1, 2. In principle, all sensor half elements 1, 2 are identical and have identical set-up or build-up, however, they are functionalized or equipped with different sensor compounds 4, 5.

In the following, we describe one possible manufacturing process for producing sensor half elements 1, 2. Subsequently, we provide one method for manufacturing the sensor assembly 12 from the sensor half elements 1, 2. Furthermore, the measurement of biological target compounds within a compound mixture 95 by means of said sensor array 12 is shown.

Sensor Compounds

Preferred substances which can be used as sensor compounds 4, 5 are oligonucleotides, which are designed as hybridization probes or specific primer sequences for solid phase PCR. One preferred class of sequences has been described in WO 2007062445 [Seitz, 2007] Herein, the oligonucleotides sequences are able to specifically react, hybridize or prime or bind with start sites of polynucleic acid analytes. Other oligonucleotides sequences are able to specifically react with the end sites of said polynucleic acid analytes. The samples, e.g. cDNA originating from RNA isolations, are modified through sequence extensions to lock those primer sequences into the start and end site positions.

The reaction of the sensor compounds with the analytes is described in section "Description of molecular recognition reactions".

Manufacturing Process of the Sensor Half Elements

In this section, the preparation or manufacturing of one sensor half element 1, 2 is described in detail. As already mentioned, it is possible to prepare each of the sensor half elements 1, 2 in the same manner, however, using different sensor compounds 4, 5 for the functionalization of the single sensor half elements 1, 2.

Each of the sensor half elements 1, 2 comprises a carrier 7. In this preferred embodiment the carrier 7 is an electrical conductor wire 74. The conductor 74 is made from copper. Of course, besides copper each metal or other electrical conducting material can be used as conductor. The diameter of the carrier 7 is about 25 µm.

In a first step, the surface of said conductor 74 is modified or layered with a thin insulating layer 82. The insulating layer 82 covers the surface of the conductor 74 and prohibits a direct electrical contact with another coated conductor 74. The thickness of the non-conducting insulating layer 82 is typically within the submicron range and forms a permeation barrier for ions. The thickness of the insulating layer 82 determines the shortest half-length of the gaps between the conductors as described later. In this preferred embodiment of the invention, the insulating layer 82 is made of polyurethane.

In the preferred embodiment, said polyurethane coating is used as insulating layer 82 and is applied to the carrier 7, 74 made from copper. The polyurethane coating forms an impermeable insulating layer 82 of a thickness of 5 µm. In principle, coatings with a thickness ranging from several µm to sub-µm can be employed. The coating is carried out through a continuous dip coating process which uses solvent diluted polyurethane enamel varnish.

Alternatively, it is also possible to use nitrides, oxides and other chalconides, self-assembled monolayers, polyelectrolyte multilayers, polymers like polyimides or fluoropolymer-copolymers, electro dipping varnishes, or others known to the art instead. Glass can also be used as insulating coating. Glass coats are available with layer thickness of 3 µm and below from GW Lab, Canoga Park, Calif., USA. Etching by hydrofluoric acid reduces the glass layer to sub-µm thickness.

Either the carrier 7, the insulating layer 82 or an additional carrier material layer 83 can contain the sensor compounds 4, 5.

In the preferred embodiment of the invention, a carrier material layer 83 is applied upon the insulating layer 82. The carrier material layer 83 is able to covalently bind the sensor compounds 4, 5. In the following example, the carrier material layer 83 contains side chains with functional groups which are compatible for cross-linking to appropriately modified oligonucleotides. Examples are 1-ethyl-3-3-dimethylaminopropyl carbodiimide EDAC to cross-link carboxy groups with amines, glutaraldehyde, bissuccinimidyl esters, diisocyanates or diacid chlorides to cross-link amines with amines, or the formation of thioether crosslink through thiol-reactive groups at amine sites by succinimidyl trans-4-maleimidylmethylcyclohexane-1-carboxylate which reacts with thiol groups.

Subsequently, the sensor compounds 4, 5 are immobilized at the surface of the carrier material layer 83. The sensor compounds 4, 5 become covalently bound to the surface via above described cross-linkers. One preferred binding chemistry is based on the self-assembly with organofunctionalized alkoxysilane molecules, which have the following advantageous features:

a. They are able to bind to various surfaces like glass, semiconductors like silicon or several metal oxides, e.g. anodized aluminium oxides layers,
b. they can polymerize to stabilize formed layers and
c. they are available with numerous functional groups like amino-groups.

Silanization is achieved by incubating the mentioned surfaces in solvents containing water which forms hydroxyl groups from oxides which in turn react with the alkoxy groups on the silanes thus forming covalent —Si—O—Si— bonds. The process creates a covalently bound interfacial layer 83 between the inorganic phase of an insulating layer 82 and the organic phase of the sensor compounds 4, 5.

Figure 3:
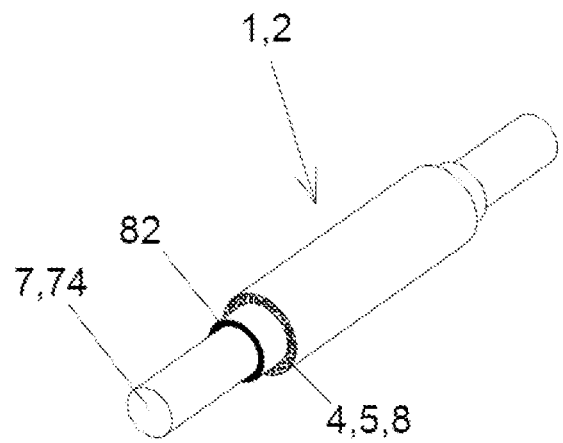
FIG. 3 shows a preferred embodiment of a sensor half element and its cross-section with an insulating layer and a carrier material layer which contains the sensor compound.

A sensor half element 1, 2 according to the preferred embodiment is depicted in FIG. 3. It consists of a carrier 7, which is covered by an insulation layer 82. The insulation layer is covered by the material layer 83 which contains the sensor compounds 4, 5. In the present embodiment the carrier 7 is a conductor 74 based on a conducting metal wire which is completely encased by the insulating layer 82 and the material layer 83.

Figure 4:
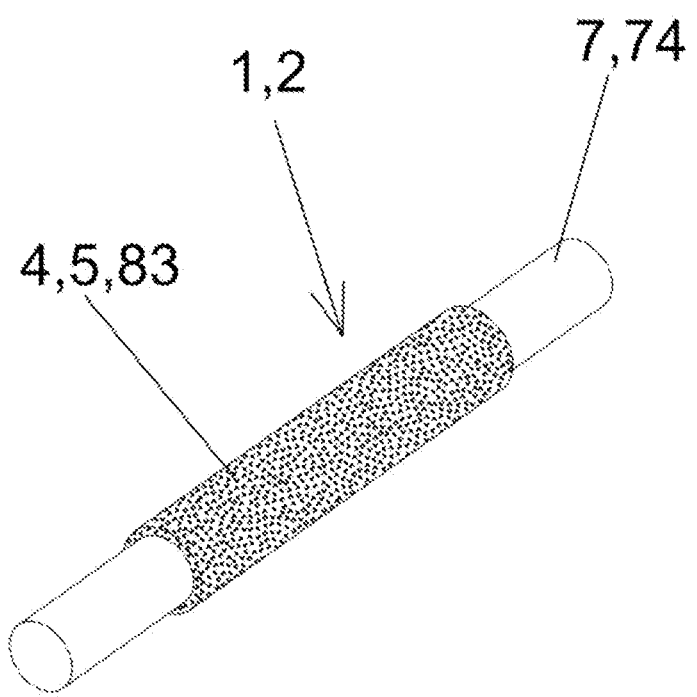
FIG. 4 shows an alternative preferred embodiment of a sensor half element and its cross-section with a carrier material layer containing the sensor compound.

Alternatively, a sensor half element 1, 2 can be prepared as shown in FIG. 4. The sensor half element comprises a carrier 7 being for example an optical conductor 74 made from optically conducting material such as glass fiber. The carrier 7 is coated with a carrier material layer 83 containing one of the sensor compounds 4, 5. The sensor compounds 4, 5 are either immobilized at the surface of the carrier 7 or at the surface of the carrier material layer 83. This embodiment does not feature an insulating layer 82.

Figure 5:
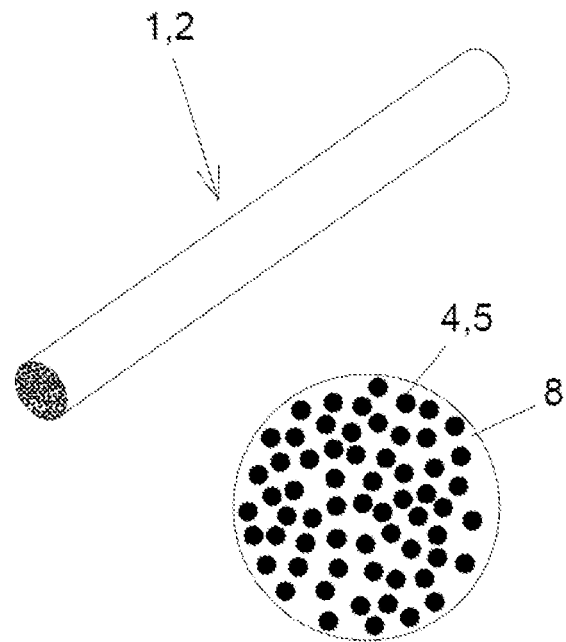
FIG. 5 shows another preferred embodiment of a sensor half element and its cross-section where the sensor compound is being part of the carrier material.

Another alternative embodiment of the invention makes use of sensor half elements 1, 2 with carriers 7 made from polymers. The sensor compounds 4, 5 are embedded in the material of the carrier as shown in FIG. 5. Sufficient numbers of sensor compounds 4, 5 are accessible at the surface so that target compounds 9 can be bound and thus be detected by downstream methods.

Alternatively, it is possible that the insulating layer 82 is directly functionalized with the sensor compounds 4, 5. Such an embodiment of the invention does not contain an additional carrier material layer 83. The insulation layer 82 itself binds or contains the sensor compounds 4, 5.

Further alternatives are that the sensor compounds 4, 5 can be embedded or bound to the carrier material layer 83 during the coating process, e.g. when the insulating layer 82 is coated with the carrier material layer 83. Sufficient amount of sensor compounds 4, 5 however remain accessible at the surface.

Alternatively, the probes can be embedded or bound to the carrier material layer 83, as long as a sufficient amount of sensor compounds 4, 5 remains accessible at the surface.

Figure 6:
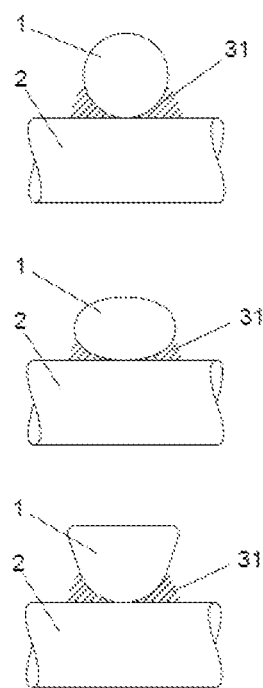
FIG. 6 shows different formations of junction areas between two approached sensor half elements in cross-section.
Figure 7:
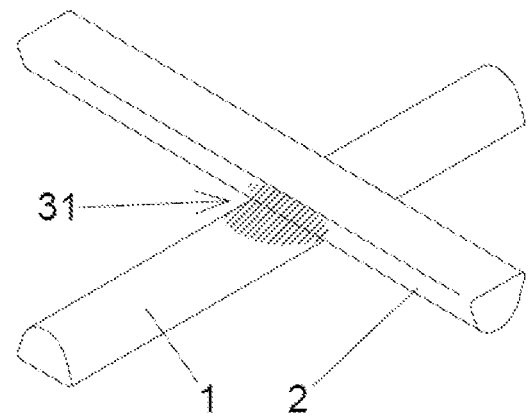
FIG. 7 shows the junction in oblique view.

The sensor half elements 1, 2 shown in FIGS. 4 and 5 feature circular cross sections. It is also possible to use other sensor half elements 1, 2 with different cross sections as shown in FIG. 6 where circular, oval and semicircular cross sections have been illustrated as examples. Important, the sensor half elements 1, 2 have at least one convexly shaped surface area for facing another sensor half element 1, 2. The exemplary junction area 31 is highlighted in FIG. 7. Accordingly and following the same principle can parts of the surface be porous and wavelike or crenatedly structured which in turn are smaller scaled and repeating convexly shaped surfaces. This embodiment is shown in the second preferred embodiment of the invention as described below.

Figure 8:
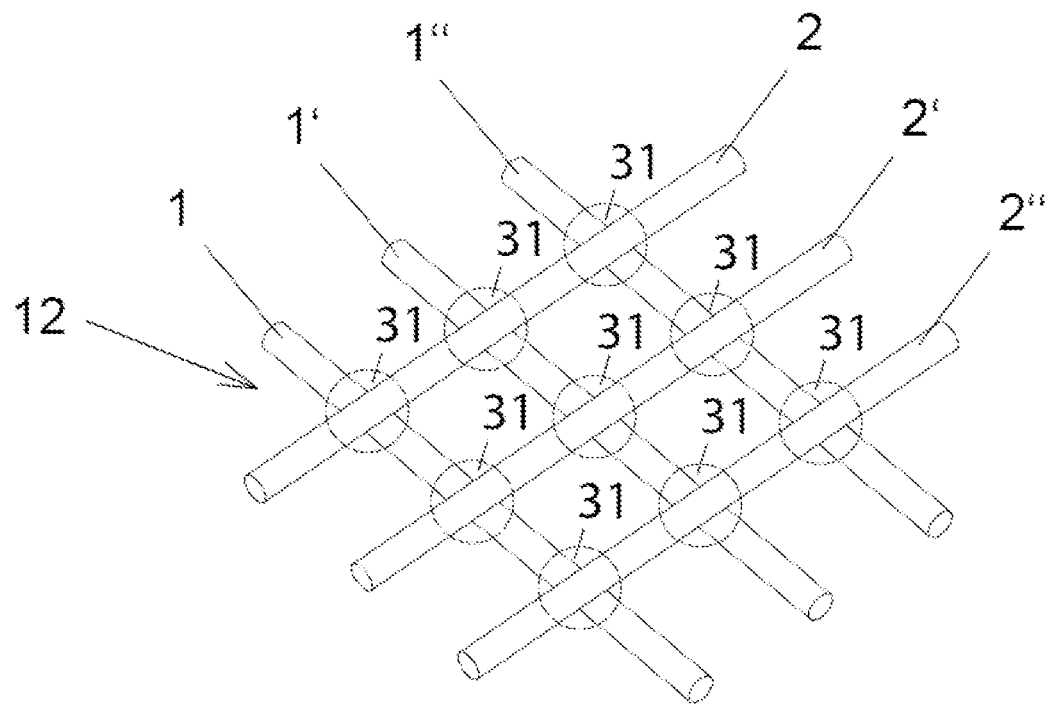
FIG. 8 shows an oblique view of a network with numerous straight aligned sensor half-elements.

Sensor half elements 1, 2 having semicircular cross sections as depicted in FIG. 6 are typically used in non-woven assemblies as shown in FIG. 8.

In the preferred embodiment of the invention can all sensor half elements 1, 2 be prepared from the same basis material and each of the used carriers 7 or conductors 74 can be individually modified using the same chemistry. The sensor half elements 1, 2 are processed separately in order to ensure that the sensor compounds remain physically separated during their immobilization.

Each of the sensor half elements 1, 2 are prepared in the above mentioned manner. Afterwards, the sensor half elements 1, 2 are assembled to the sensor array 12, which has the form of a network as shown in FIG. 1.

Alternatively, it is also possible to use different basis materials and/or different binding chemistry. For instance, different organic molecules like amino or carboxy compounds can be chosen to insert lateral spacers at the surface of row elements 1 and column elements 2 to provide sensors 3 or junction areas 31 with defined surface charge asymmetries.

Making of a Woven Conductor Network Sensor Array

The preferred embodiment of the invention comprises many row elements 1 and many column elements 2, and is exemplarily shown in FIG. 1 with two times three sensor half elements 1, 2. The individual sensor half elements 1, 2 are interlaced and woven. Consequently, the sensor array 12 comprises nine junction areas 31 and nine sensors 3.

Alternatively, such sensor arrays 12 can be obtained by knitting or otherwise hitching the sensor half elements 1, 2 into a fixed net structure with tight junction areas 31 which is not shown in the figures.

The sensor array 12 according to the first preferred embodiment features a rather simple woven network. As already mentioned, the row elements 1 and column elements 2 of the preferred embodiment comprise a carrier 7 which is a conductor 74 made of electrically conducting material. Each junction area 31 of intersecting sensor half elements 1, 2 defines an electrical device, namely a sensor 3. The junction area 31 between two sensor half elements 1, 2 as well as the resistance or conductance of the sensor 3 is defined by the geometry of the conductors 74, such as their size, curvature and the type of their twist or interlace.

Figure 9:
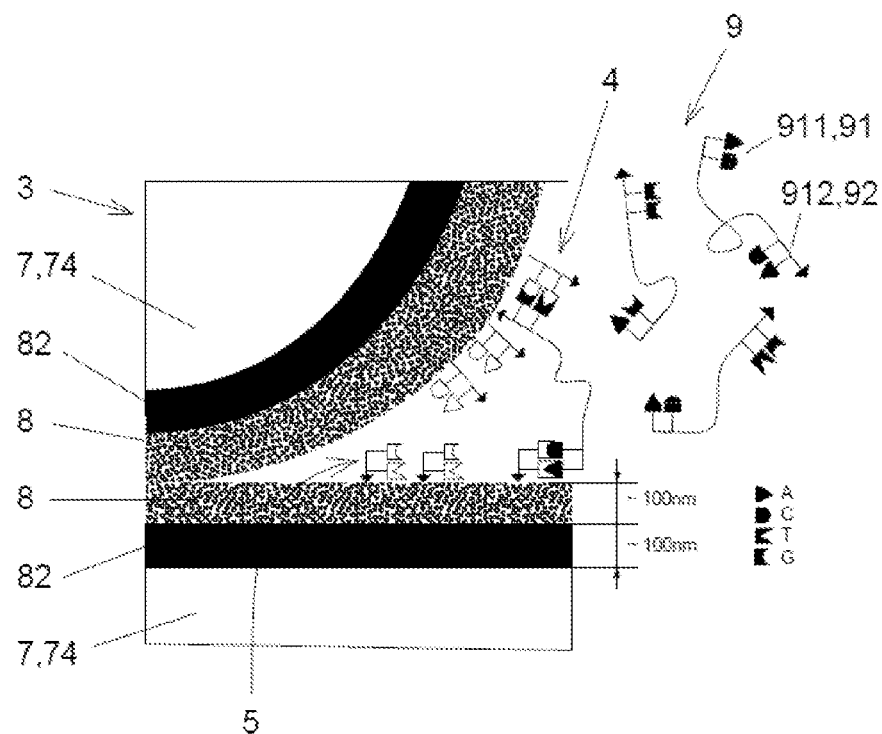
FIG. 9 shows the geometry of a junction area and a sensor formed between two sensor half elements, with the principle reaction scheme of dual hybridization.

The minimum distance between the respective carriers 7 sensor half elements 1, 2 is also referred to as the gap size between two sensor half elements 1, 2. FIG. 2, and in more detail FIG. 9, shows the geometry of a sensor in the junction area between two sensor half elements. In the preferred embodiment of the invention the carrier material layers 83 of the opposite sensor half elements 1, 2 touch each other and the total shortest distance between the two conductors 74 of the sensor 3 is determined by the sum of the thicknesses of the insulating layer 82 and the carrier material layer 83 of both sensor half elements 1, 2. As the sensor half elements 1, 2 are manufactured according to the same manufacturing process the gap size is twice the thickness of the overall coating of the sensor half elements 1, 2. The electrical properties of the sensor 3 depend on geometry of the junction area of the respective sensor half elements 1, 2.

An alternative arrangement of the sensor half elements is shown in FIG. 8. Here a plurality of straight row elements 1 and line elements 2 are shown that touch each other in single points respectively. The space around the physical contacts form the junction areas 31 which define tiny gaps. The gaps are opening to, and accessible from, the outer side.

The woven structure, FIG. 1, can be produced as two dimensional structure of arbitrary size and can be optionally folded afterwards, e.g. in cylindrical shape. Another preferred woven structure can be directly produced as a 3D mesh, e.g. covering a tubular surface. This alternative embodiment of the invention is advantageous, because the sensor array 12 can be more easily integrated with for example fluidic systems.

Another alternative embodiment of the invention comprises sensor half elements that cross, intersect, converge or approach each other more than once. The signal intensity, for instance the change in capacitance or the conductance of the sensor 3, increases with the number of identical junctions areas 31 formed between two sensor half elements 1, 2.

Typical alternatives of the invention concern sensor arrays with about 1000 row elements 1 and about 1000 column elements 2.

The distance between individual junctions 31 depends on the electrically conducting carrier 74, mainly on its diameter and flexibility. Wires of a diameter of 50 μm are used to allow approximate densities of $4.4 \times 10^3$ sensors per $cm^2$ when the inter-wire spacing is set to the 2-fold of the diameter.

Wires 74 as small as 10 μm, e.g. from Johnson Matthey, Noble Metals, UK, are in the same order of magnitude as silk and carbon fibers and allow integration densities of up to $1.1 \times 10^6$ $cm^{-2}$. Nanofibers which are made trough e.g. electro-spinning can be produced in the submicron range and eventually woven into structures with junction densities of up to $10^6$ $cm^{-2}$.

For obtaining the structure a weaving process is used which is described below: For the weaving itself one group of the sensor half elements 1, 2, e.g. all column elements 2, used as warps and the remaining row elements 1 are used as wefts. The individual warps, i.e. the column elements 2, are mounted at one end into a contacting frame circuit board by soldering. The other site remains mounted to the mini loom and can be moved separately. The wefts, namely the row elements 1, are successively mounted into the structure through the mini loom and mounted on both sites to the contacting frame circuit board. Finally, the free ends of the warps are mounted into place and the whole assembly is finished.

Alternatively, larger looms are employed to make multiple sensor array weaves which are separated through appropriate gaps. In a second step the individual sensor arrays are cut and transferred onto contacting frame circuit boards while mounted through soldering.

Assembly of the Measurement Cell

The preferred embodiment of the invention comprises a measurement cell 150 which provides the enclosure and contacts. The sensor array 12 of m×n individual sensors 3 becomes connected via the m+n conducting sensor half elements 12, which counts up e.g. to 2000 connections which address 1 Mio sensors. This principle enables the rather simple connecting of high density sensor arrays. In contrast, if each junction area 31 is connected by two separate conductors the number of those conductors would increase linearly with the number of sensor fields in the array and lead to 2 Mio contacts for 1 Mio sensors. High contact number socket technology is established up to the order of thousands in semiconductor testing. High contact number sockets of the current industry standard combine 49×49 spot contacts and can accommodate comfortably said 2 times 1000 contacts to the sensor half elements 1, 2.

The frame is a multilayer circuit board made from up to 12 individual circuit boards which translate the 2 rows of up to 1000 narrowly spaced line contacts into a matrix of spot contacts according to the high contact number socket.

An enclosure embeds the frame which supports the sensor array and encloses the reaction volume which is accessible through microfluidic connections. The complete assembly is the sensor cell 150.

Description of Molecular Recognition Reactions

Each sensor 3 is formed by one gap that carries two different sensor compounds 4, 5, one at the surface of each sensor half element 1, 2. The sensor compounds 4, 5 are e.g. short oligonucleotides like hybridization probes or primers which are immobilized and exposed at the surface of the sensor half-element.

A schematic view of a junction area 31 is shown in FIG. 9. The figure does not represent the correct spatial relationships between the conductor 74, which has a diameter of about one to several μm, the coatings 82, 83 with a thickness within the submicrometer and nanometer range, and the exemplary sensor compounds 4, 5 and analytes 9 such as cDNA molecules in molecular dimensions. The latter have typically an average length of 2500 nucleotides and are approximately 0.85 μm long.

The basic principle of the sensor action is a molecular recognition reaction between the analytes 9 under investigation and the sensor compounds 4, 5. Several kinds of reactions are possible which are for example, a. hybridization FIG. 9, b. hybridization and amplification FIG. 10.

Figure 10:
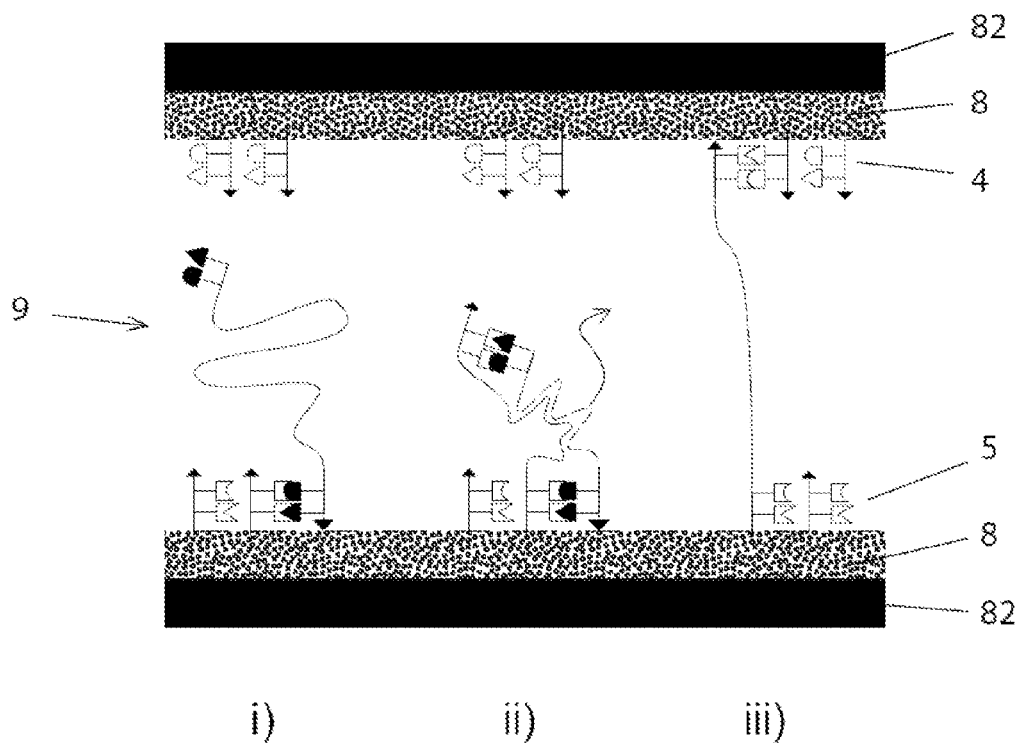
FIG. 10 shows the schematic cross-section of one general junction of sensor half-elements with the principle amplification reaction scheme.

FIGS. 9 and 10 show schematic representations of the reactions a, and b. The symbols indicate a certain nucleotide of A, T, G or C which are able to match the complementary nucleotide. The filled symbols are the analytes whereas the hollow symbols stand for the sensor compounds or reaction products. The arrows indicate the 5'→3' direction of the oligo- and polynucleotides.

a) Hybridization:

Sensor 4, 5 compounds are oligonucleotides which are immobilized with their 5'-site at one group of sensor half elements, e.g. all row elements 1 shown as the top element in FIG. 9, and with their 3'-site the opposite column elements 2 shown as the bottom element in the same figure. When a polynucleotide mixture 9 enters the sensor array molecules are able to hybridize to the sensor compounds 4, 5 as shown in FIG. 9. Analytes are able to hybridize at the 3'-, 5'- or both sites. The hybridization buffer, containing e.g. de-ionized formamide, Denhardts, Tween, SDS, dextran and DEPC, the temperature and time are optimally chosen for sequence specific dimerization and trimerization. Such conditions are e.g. 57° C. for 1 h. During this period the solution is kept in a moving state to accelerate primarily slow diffusion rates into the surface and gap region. The final hybridization is the equilibrium binding state. Not hybridized polynucleotides can be removed through washing steps. The result is a segregated analyte pattern in the sensor array.

The sensor compounds are preferably positional locked, which means that additional sequences allow the sensor compounds 4, 5 to hybridize to the start 911 or end 921 sequence of the analytes only. The additional sequences are introduced at the anchor site of the sensor compound. The consequence is that much shorter sequences can be used to obtain a noticeable segregation. For example, each longer analyte nucleotide sequence has anywhere in their chain at least one adenosine, A, but only one quarter in average starts with one A. This principle applies to each nucleotide position.

b) Hybridization and Amplification:

Sensor compounds 4, 5 are primer oligonucleotides, which are all immobilized with their 5'-site as shown by sketches in FIG. 10.

In a first step i, polynucleotides of the analyte mixture 9 entering the sensor array 12 and hybridize to those sensor compounds 4, 5, i.e. primers, which are complementary to their 3'-side. The hybridization buffer containing deionized formamide, Denhardts, Tween, SDS, dextran and DEPC, the temperature and time are optimally chosen for sequence specific dimerization, e.g. 57° C. for 1 h. During this period is the solution kept in a moving state to accelerate primarily slow diffusion rates into the surface and gap region. Not hybridized analytes 9 can be removed through washing.

In a second step ii, an assay with activated polymerase, Taq, Pfu, Phusion or similars, single nucleotides dNTP's and additives like divalent cations and stabilizers are applied to perform a single elongation 70° C. for 2 min. The reaction results in bound complementary copies of the templates along the electrodes according to the sequence and proportional to the starting concentration. Through stringent washing will the dsDNA be denatured and the original template can be removed leaving the covalently bound complementary sequence behind.

In a third step iii, an assay with polymerase, dNTP's and additives will be applied and a controlled polymerase chain reaction is performed through thermocycling, e.g. 50 cycles of 95° C. for 30 sec, 57° C. for 30 sec and 70° C. for 2 min. Only those polynucleotides can be amplified which find complementary primers at the opposite surface [Seitz, 2007].

The hybridization method, a), is simple as no additional enzymatic reaction and no fast thermocycling is required. The hybridization and amplification method, b), is technically more sophisticated but provides two advantages. First, the proof-reading function of the polymerases enables to correct for mispriming events. Second, the amplification multiplies the amount of analyte 9 in the junctions 31 through the generation of identical copies.

The biochemical molecular recognition fulfilled the first part of the sensor reaction. It detects the analyte 9 and segregated it into different subpools. It means that each sensor 3 contains predominantly molecules with sequences corresponding to both sensor half elements. A real time or endpoint measurement only identifies the amount of material in each sensor.

With regard to the subsequent electrical characterization can further signal enhancements be achieved through post labeling with materials which possess strong interaction with alternating electric fields like conjugated polymers, metallic nanoparticles and others.

Electrical Characterization of Junctions

Because the carrier of the sensor half elements 1, 2 is conductive each junction 31 can be electrically addressed through both of the connecting sensor half elements 1, 2 themselves. The junction areas 31 act as capacitors which are able to sense the dielectric properties of the compounds in the gap region or the sensor 3. Each junction area 31 can be envisaged in a first approximation as a parallel alignment of tiny plate capacitors of different width and area which enclose small partial volumes adding all up to the total active surface and volume. The change of each capacitance is proportional to the change of the dielectric hence relative static permittivity or dielectric constant, $\in_r$. The detection of the capacitance occurs through sending a timely variable electrical signal, e.g. voltage steps and pulses, AC potential or current, along one conductor and recording the response at the other conductor.

Figure 11:
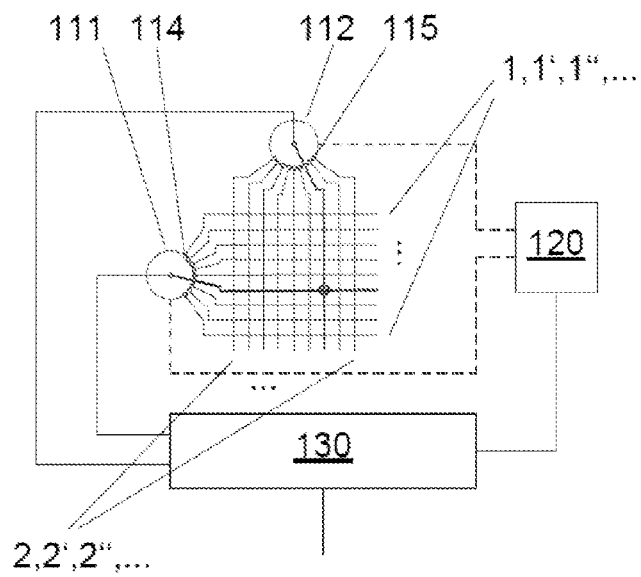
FIG. 11 shows the evaluation circuit for the electrical detection of the concentration of the compounds under investigation.

FIG. 11 shows the evaluation circuit 100 comprising a first selection unit 111, e.g. an analog multiplexer, with one primary port and a plurality of secondary ports 114 which are individually connected to one row element 1 each, a second selection unit 112 with one primary port and a plurality of secondary ports 115 which are individually connected to one column element 2 each. The circuit 100 further comprises a control circuit 120 which controls the two selection units 111, 112. The first selection unit 111 selects one of the row elements 1 and the second selection unit 112 selects one of the column elements 2. The measurement circuit 130 quantifies the electrical impedance between the main ports of the addressing circuits 111, 112. Each combination of a column element 2 and a row element 1 enables one distinct sensor 3 formed between the respective selected sensor half elements 1, 2. The impedance of the addressed sensor 3 is measured by measuring the impedance between the primary ports of the selection units 111, 112. Sensor half elements 1, 2 next to the addressed combination of sensor half elements 1, 2 are held or fixed to a constant potential, e.g. floating ground. All sensors 3 are measured in consecutive or any other order.

It is possible to analyze several sensors 3 in parallel by addressing one row sensor half element 1 and several column sensor half elements 2, and vice versa, by employing a number of further selection units 111, 112 and measurement circuits 130.

After the measurement, it is possible to visualize the measured capacitances or impedances. For means of visualization, a digital image can be rendered, wherein each of the pixels of the image is assigned a value corresponding to the measured impedance or capacitance. The grid arrangement of the sensors 3 within the sensor array 12 equals to the grid arrangement of the pixels within the digital image.

Figure 12:
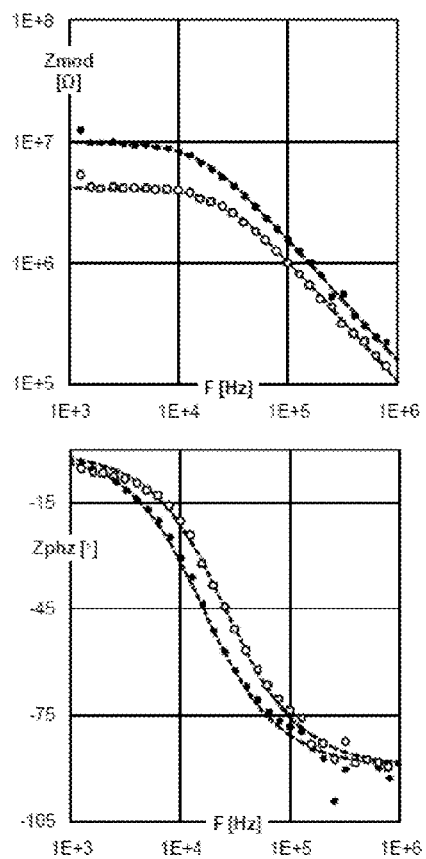
FIG. 12 shows the Bode diagram of impedance spectra of two central neighbouring net junctions in water with one junction, hollow dots, being modified by silicon grease.

In this preferred embodiment of the invention, the measurement unit 130 is a combination of potentiostat and frequency analyzer that records amplitude and phase shift of the response signal in comparison to the entrance AC signal. Typical impedance spectra are shown in FIG. 12 and depict the impedances at different frequencies. Impedance spectra can be used to characterize the substances being bound to the respective sensors 3. Oscillator, charge and AC bridge based approaches are in use to determine capacitances, whereby the charge based capacitance measurement technique, CBCM, is the simplest realization [Chen, 1996]. AC bridge based commercial instruments and circuit designs are available to measures capacitances with 1 fF resolution. Beyond this resolution, potentiostats have been presented to approach the 10 aF range [Carminati, 2009].

Figure 13:
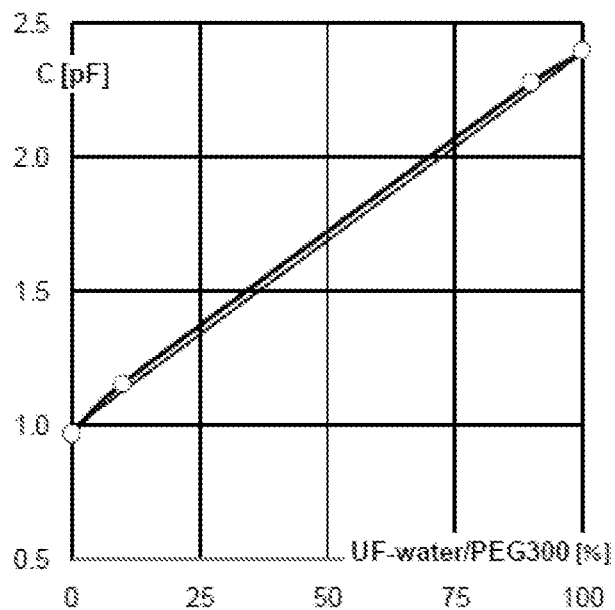
FIG. 13 shows the gap capacitance as a function of water-PEG300 ratio of the cell solution using a junction of insulated copper wires.

It might be not always necessary to determine capacitances or impedances through modulus and phase shift. Under equilibrium conditions both values can be transformed into each other. Furthermore, if a phase shift is seen to be known it might be enough to determine the modulus and calculate the capacitance using a valid equivalent circuit. By these means is it possible to use single frequency measurements to determine valid capacitances. A representative calibration curve is shown in FIG. 13.

The impedance or capacitance is either determined by end point measurements or by using real time measurement. Real time measurements are able to characterize the temporal behavior of the electrical properties of the sensors during the molecular recognition reactions. Real time therefore enables to follow hybridization kinetics and amplification rates during thermocycling depending on the type of experiment.

Numerical Determination of Analyte Concentrations

Impedance spectra show the dependent responses of all individual components in the circuit which are predominantly the gap capacitance, but also the capacitance of the double layer of the residual sensor half element surface outside the junctions 31, the resistances of the charge transfer across the conductor-solution interface and the solution itself, and inductivities as function of the AC frequency. An appropriate equivalent circuit allows fitting the impedance spectra to extract the values for the individual circuit components. Contributions of the capacitance of the residual double layer are minimized through the shielding of the neighbouring sensor half elements which are held at constant potential. The solution resistance is maximized through low ionic strengths and geometry of the measurement cell, e.g. thin liquid films.

Dual hybridizations as shown in FIG. 9, or priming followed by amplification reactions as shown in FIG. 10 change the molecular ratios of the molecules in the junctions 31. The accumulation of DNA, hence analyte and/or copies of the analyte, increase the local concentration and lead to a displacement of water and buffer compounds in the junction areas 31. The remaining water and ions of the buffer become increasingly structured. The relationship between DNA concentration and capacitance is determined through a calibration curve as exemplarily shown in FIG. 13 for another polymer, here polyethyleneglycol 300, PEG300.

Water has a relative dielectric constant, $\in_r$, of 80 and 1% DNA solution exhibits values of more than 90, values recorded at 1 MHz [Takashima, 1984]. In first approximation, each sensor 3 can be envisaged as a parallel alignment of tiny plate capacitors of different width and area, which add all up to the total active surface area and volume. A 50 µm wire cross junction forms a total cross-section of $2.5 \cdot 10^{-9}$ m². With an insulating layer 82 of 0.1 µm thickness, the minimal separation of both sensor half elements 1, 2 is 0.2 µm. Using the following equation with 10 equal steps and $\in_r$ of water with 80, the total capacitance approximates to 192.1 fF.

$$C = \sum_{i=1}^{n} \varepsilon_0 \varepsilon_r \frac{A_i}{d_i}$$

Let's now assume that the most inner part of the junction is defined through the first $10^{th}$ of the distance and area changes its dielectric properties due to an accumulation of DNA following above described molecular recognition reactions. If $\in_r$ of this section changes from 80 to 90, the capacitance increase to 200.3 fF.

Sensor Array Processing and the Readout Device

A central part of the processing and readout machine 160 is a high contact number socket with thermo-controlled lid, a control circuit 120, a measurement circuit 130 and a microfluidic system. The readout machine 160 is controlled by a computer.

One blank sensor cell 150 is loaded to the readout machine 160 by placing the sensor cell 150 into the high contact number socket and closing the lid. By closing the thermo-controlled lid, inlets and outlets to the microfluidic system of the machine are thermally connected. The following three steps are carried out.

First, one initial washing and equilibration step with buffer solution is carried out to condition the cell 150. A baseline or reference measurement is taken.

Second, the sample, e.g. cDNA, which has been obtained from RNA tissue sample preparation and reverse transcription, is injected.

Third, the program performs an initial annealing, following washing and thermocycling steps according to the scheme shown in FIG. 10. After each thermocycle the impedances of all junctions are measured and recorded.

Impedance changes are evaluated to calculate concentration values for the amount of DNA which has been amplified in each sensor 3 during the cycles. In analogy to real-time PCR are concentrations determined from the evaluation of the amplification curves. The signals which are measured with each sensor 3 represent the amount of a class of cDNA molecules which have been captured in the junction area 31 of the respective sensor 3. Those DNA molecules are characterized through the binding sites which are complementary to the two sensor compounds.

Second Preferred Embodiment

Sensor Arrays with Common Carrier Plates

Figure 14:
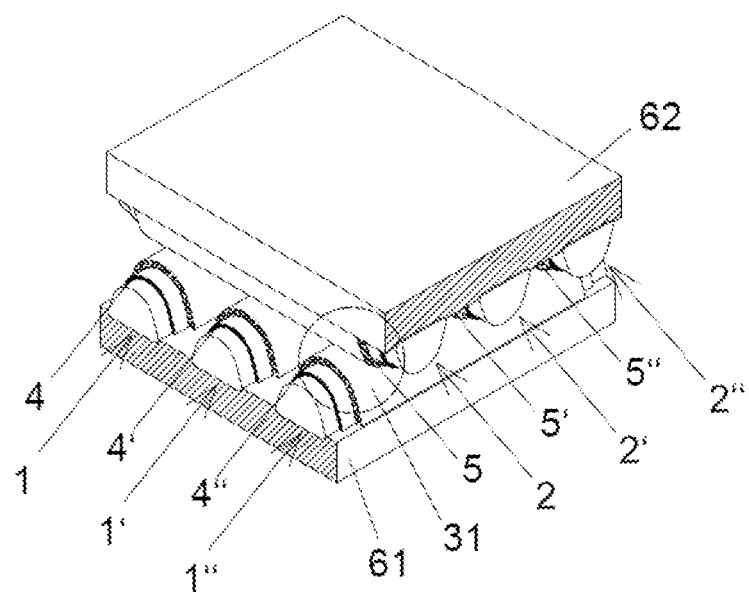
FIG. 14 shows the central part of a sensor array assembly with two common carriers which support three sensor half elements each to form nine individual sensors.

The second preferred embodiment describes structures which are fabricated through arranging and aligning sensor half elements 1, 2 on one of two common carriers 61, 62 as shown in FIG. 14.

Figure 15:
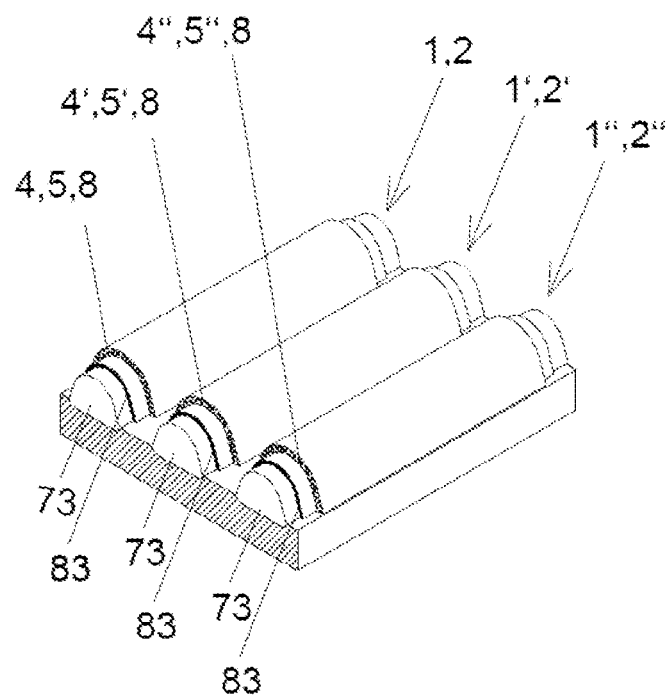
FIG. 15 shows an alternative preferred embodiment of a common carrier with three general sensor half elements.

The sensor half elements 1, 2 are functionalized according to the method of functionalization as described above. Each of the row elements 1 is arranged and aligned on the first common carrier 61, each of the column elements 2 is arranged and aligned on the second common carrier. The sensor half elements 1, 2 are supported by the respective common carrier 61, 62. In this preferred embodiment of the invention, the row elements 1 are arranged in parallel on the first common carrier 61 and the column elements 2 are arranged in parallel on the second common carrier 62. One of the common carriers 61, 62 is depicted in FIG. 15. The row elements 1 and the column elements 2 are aligned perpendicular to each other. The parts of the surface of the row elements 1 and column elements 2 that face each other are porous, wavelike structured or crenated. Such sensor half elements 1, 2 are advantageous, because the surface area of the junctions 31 available for binding is increased. Accordingly, the sensitivity of the sensor is improved.

The functionalization of the sensor half elements can be carried out before arranging the sensor half elements 1, 2 on the common carriers 61, 62 or alternatively thereafter. Either way, the functionalization occurs before assembling the common carriers 61, 62 to one unit as shown in FIG. 14. During this assembly process are the first common carrier 61 and the second common carrier 62 approached to each other so that the orientation of the row elements 1 and the column elements 2 are fixed, in this preferred embodiment with an angle of 90 degrees, FIG. 14. The row elements 1 and the column elements 2 face each other or contact each other.

The Making of Structured Common Carriers

The common carriers 61, 62 are made from metal coated silicon wafers through a standard photolithographic process. The preferred design consists of 1000 parallel conductors 74 of 2.5 cm length and 20 μm width which are separated by 5 μm. The conductors 74 are arranged on a square shaped area on the respective common carriers 61, 62. The square shaped areas have an edge length of 2.5 cm.

In a first step, the sensor half elements 1, 2 are structured on the common carriers 61, 62. The conductors 74 having the form of a cylinder with a semicircular cross section, FIG. 15. The conductor length, width and spacing can be easily adapted to the number of sensor half elements 1, 2 and the number of required sensors.

Figure 16:
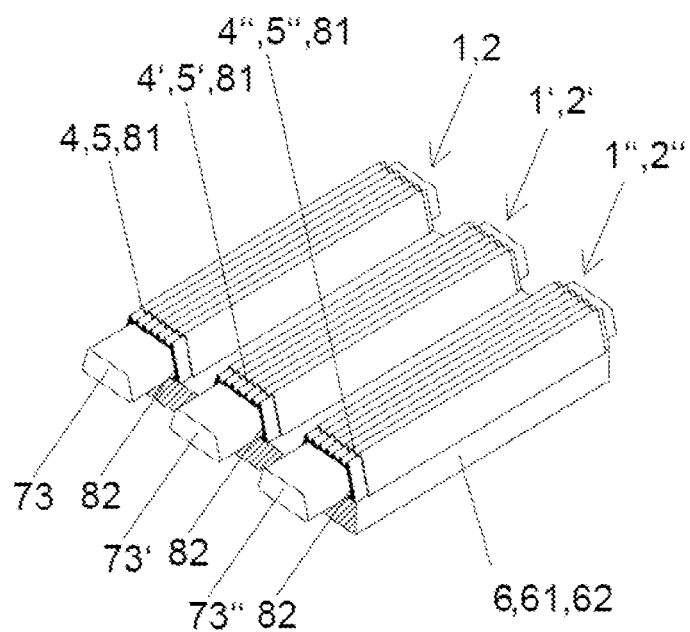
FIG. 16 shows one alternative embodiment of the common carrier with sensor half elements which possess a wavelike surface structure.
Figure 17:
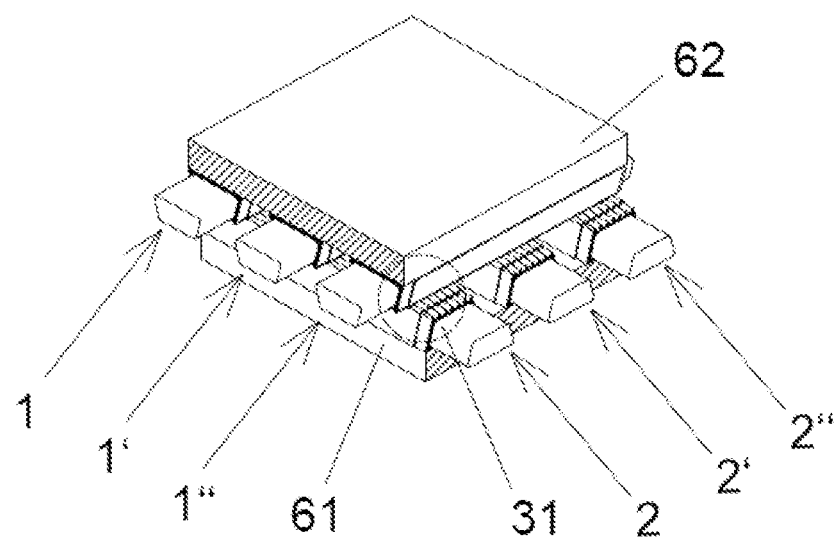
FIG. 17 shows the central part of a sensor array assembly with two common carriers which support three sensor half-elements each possessing a wavelike surface structure to form nine individual sensors.

Alternatively, the shape of the sensor half elements 1, 2 which are created on the common carriers 61, 62 may alter. An alternative preferred embodiment, shown in FIG. 16, comprises trapezoidal conductors 74 each of which having a crenated surface. The crenated surfaces of the conductors 74 are coated with an insulating thin layer 82 or film by sputtering as part of the same lithographic process. The sensor half elements 1, 2 are arranged in a manner that the crenated surfaces of the row elements 1 are facing and approaching or touching the crenated surfaces of the column elements 2 as shown in FIG. 17.

The photolithographic process is also used to integrate the selection units 111, 112 or multiplexers 111, 112, as described in the first preferred embodiment, into the common carriers. The layout ensures that the conductors 74 are connected to the selection units 111, 112 as shown in FIG. 11.

Figure 18:
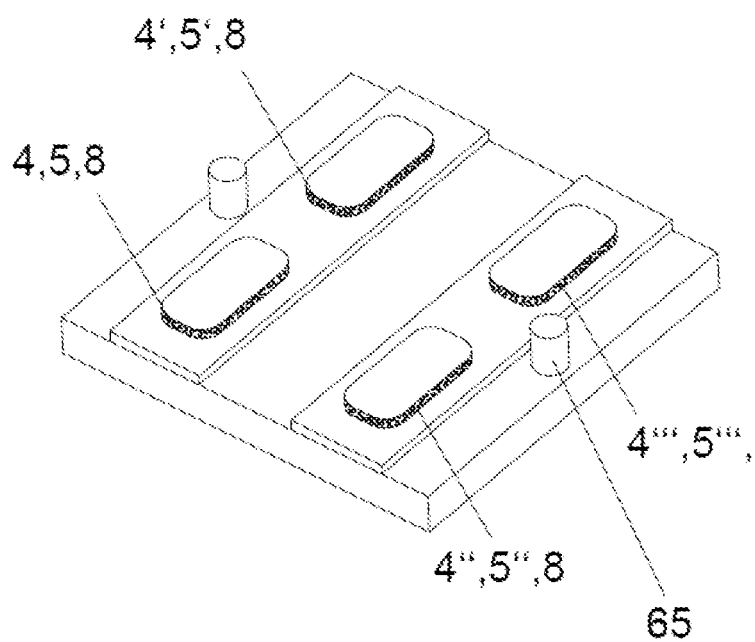
FIG. 18 shows an alternative preferred embodiment of a common carrier with two aligned sensor half elements, two functionalized surface regions and two spacer elements.

Another alternative preferred embodiment uses a common carrier 6 and spacer 65 assembly where the spacer elements have been integrated into the common carrier plates as it is shown in FIG. 18. The surface of the sensor half elements 1, 2 does not necessarily have to be convexly shaped or crenated. In the preferred embodiment the surface is entirely flat. The spacers 65 have a predefined thickness to prevent the sensor half elements 1, 2 from touching each after the assembly of the complete sensor cell 150, FIG. 19. The spacers 65 fulfill two functions, namely to firstly create a tiny gap which allows the analyte to enter the gap region and second, to prevent the conductors 74 from touching each other and therefore to avoid short circuits. Even though the passivation and/or insulation of the conductors 74 is possible, those sensor half elements 1, 2 do not require an insulation layer 82.

Functionalization of the Sensor Half Elements

Sensor compounds are either alike the sensor compounds which have been described in the first embodiment, oligonucleotides designed as hybridization probes or primers. In addition, antibodies, which are globular plasma proteins of high variability, can be used. For this preferred embodiments of the invention. The hypervariable regions of the antibodies are directed to corresponding antigens.

The sensor half elements 1, 2 are functionalized by using the same chemistry as described in the first preferred embodiment of the invention. If the carriers 7 of the sensor half elements 1, 2 are aligned on the common carriers 61, 62 before their functionalization, the method of functionalizing requires a precise lateral resolution of the same dimensions as the sensor half element assembly. In order to obtain such lateral resolution, three technologies fulfill those requirements.

Firstly, standard piezo plotters with spot sizes at around 100 μm are able to deposit the sensor compounds 4, 5, one to the respective carriers 7. Incubation at constant humidity and elevated temperatures, e.g. 60° C., facilitates the covalent binding. After the binding reaction, any surplus sensor compounds which were have not bound to the surface are removed by flushing with blocking and washing solutions.

Secondly, for line widths below 50 μm DNA probes can be directly synthesized to the respective carriers 7. This process is directed by lithography and uses photo-activatable linkers and is a standard technology in microarray production. Only the sensor substances 4, 5, e.g. sequences of the DNA probes, which are specific to the individual sensor half elements 1, 2 have to be synthesized at the surface. Common sequence motives of the sensor compounds 4, 5 can be synthesized in bulk and immobilized to the insulating layer 82 or carrier material layer 83. Such pre-cursor compounds can be applied unison to many or all carriers 7 at once.

Alternatively, it is also possible to modify all or groups of sensor half elements 1, 2 first with pre-cursor compounds. Afterwards, the remaining nucleotides are synthesized step by step in situ. Because the genetic code contains only four different bases only four different stamps are required, each of which having one reactive nucleotide to synthesize one specific nucleotide position. Each reaction is followed by a washing and new activation step.

It is also possible to immobilize a number of precursor compounds, e.g. 64 with three selective nucleotides. Afterwards, further nucleotides are synthesized in situ at the surface step by step.

Thirdly, microfluidic stamps can be used to modify the carriers 7. Such stamps contain microfluidic channels which are filled with the sensor compounds 4, 5. For instance, the stamps contain 64 channels. A number of 16 such stamps comprising 64 channels respectively are used in line to modify up to 1024 sensor half elements 1, 2.

Assembly of Two Plates to One Measurement Cell

Two common carrier plates 61, 62 with the sensor half elements 1, 2 and the addressing circuits are assembled by stacking two separately functionalized common carrier plates 6 and sealing the assembly. The structure or the common carrier plates are nearly identical. The common carriers 61, 62 are aligned perpendicular to each other so that the sensor half elements 1, 2 of two approaching common carriers 61, 62 are also perpendicular to each other.

Figure 19:
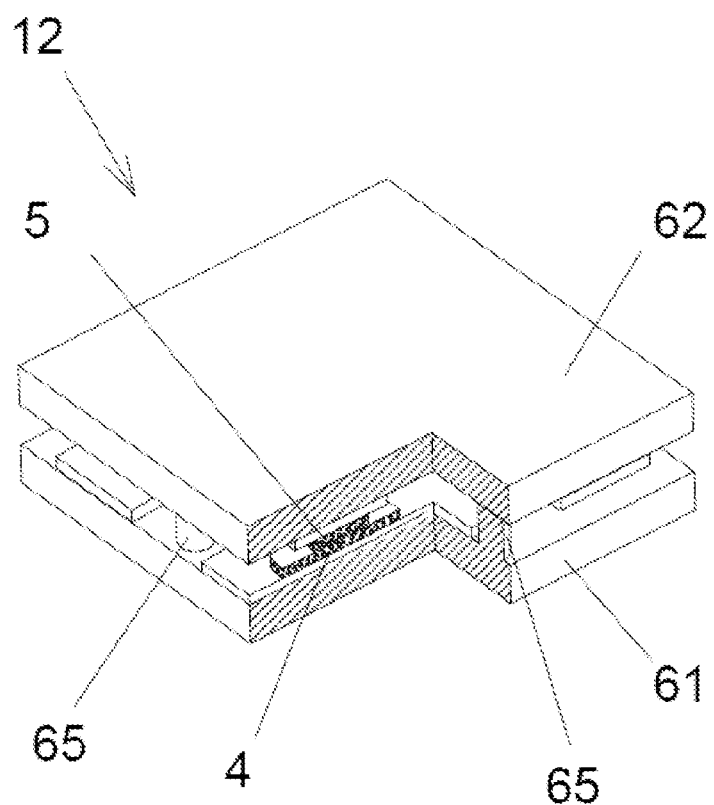
FIG. 19 is an oblique view of a sensor array assembly containing spacers with two common carriers which support two sensor half elements each to form four individual sensors.

Sections of such assemblies are shown in FIGS. 14, 17 and 19. In all cases the common carrier plates 61, 62 are pressed together. The sensor half elements are either touching FIGS. 14 and 18 or not in contact to each another, FIG. 19. A short circuit is prevented by insulating layers 82, or alternatively, by using two common carrier plates with integrated spacer elements 65. The two plates are assembled in a similar fashion and perpendicular tilted as shown in FIGS. 17 and 19.

The cartridge-like measurement cell 150 is completed by attaching microfluidic ports, not shown in the figures, and sealing the edges around the assembled common carrier plates 61, 62.

The processing, reaction steps and measurement of the cell 150 is identical to the respective steps of the first preferred embodiment of the invention.

Further Embodiments

In the following, alternatives and variations of the invention are described.

Alternative Making of Conducting Sensor Half Elements

According to a first alternative of the invention, the carriers 7 are conducting wires 74 made of metal like copper, gold or other suitable alloys having the same or higher electrical conductivity. High specific conductivities are advantageous, because for a high degree of integration are the conductors preferably thin and long. Sensor compounds 4, 5 are polymerized into the outer layer of the insulating coating 82.

For this purpose, polyamide layers are made from hexadiamine and oligonucleotide-diamine and adipoylic acid through interfacial polymerization [Horn, 1989]. The conducting wires cross the interface between one non-mixable aqueous and one organic solvent, each containing one of the compounds. The aqueous phases contain branched bi-functionalized oligonucleotides. The coating forms a nylon-like layer. One such interface is suitable to coat long quasi-continuous wires, which then are collected onto mandrels. The same setup can be used to functionalize many conductors in series. Only the bi-functionalized oligonucleotides are changed to produce a new sensor half-element.

According to a second alternative of the invention, the carriers 7 can be made from aluminium wires with thicknesses in the order of 10 to 50 μm being anodized to form an insulating layer 82. Current density, time and the anodizing solution determine the density and thickness of the oxide layer. Then, through the reaction of organosilanes such as 3-aminopropyltrimethoxysilane or N-2-aminoethyl-3-aminopropyl-trimethoxy-silane with hydroxyl groups, which have formed from the most outer oxide layer in aqueous phase, amino functionalizations are introduced. Those allow for the binding of appropriate oligonucleotides trough cross-linking reactions as described above.

According to a third alternative of the invention, the carriers 7 can be made from carbon fibers being chemically oxidized at the surface to gain a high density of carboxyl groups [Zielke, 1996]. Those carboxyl groups anchor crosslinkers like EDAC. The amine modified oligonucleotides contain a molecular spacer which can be cross-linked afterwards to form an impermeable interface between the carbon fiber and the oligonucleotides.

Examples: Sensor Half Elements Surface Structuring

The extent of surface interaction can be enhanced through additional soft matter coatings which are grouped in the category carrier material layer 83. Polymers, in particular gels, are suitable to form a coating which can be squeezed. Such coatings contain binding sites to covalently bind the sensor compounds 4, 5. The junction area 31, i.e. the region between two sensor half elements 1, 2 where molecules 9 under investigation can bind to each of the sensor compounds 4, 5 with two of its binding sites 91, 92, can be increased by using said gels. Dendrimers like polypropylenimine polyamine range from tetraamines to tetrahexacontaamines and can be chosen to build 3D-like structures with higher interface densities of the sensor compounds 4, 5.

Figure 20:
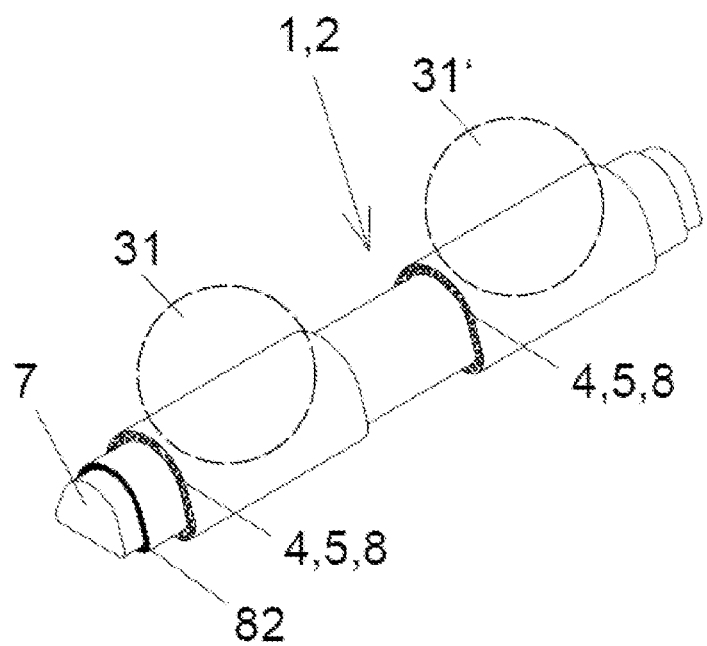
FIG. 20 shows one sensor half element where the sensor compound is contained in separated regions.

FIG. 20 presents a sensor half element 1, 2 which is supported by a carrier 7 and coated by an insulating layer 82. The sensor compound 4, 5 is embedded in a carrier material layer 83 and is applied periodically in regions or separated areas 76, 77. The position of the junction areas 31 is defined by the position of the separated areas 76, 77 of the sensor half elements 1, 2. The resulting design combines two advantages. First, less sensor compounds 4, 5 are required to produce the individual sensor half elements 1, 2. Second, the surface regions outside the junction areas 31, where the analyte could be trapped without contributing to the measurement, are minimized.

Figure 21:
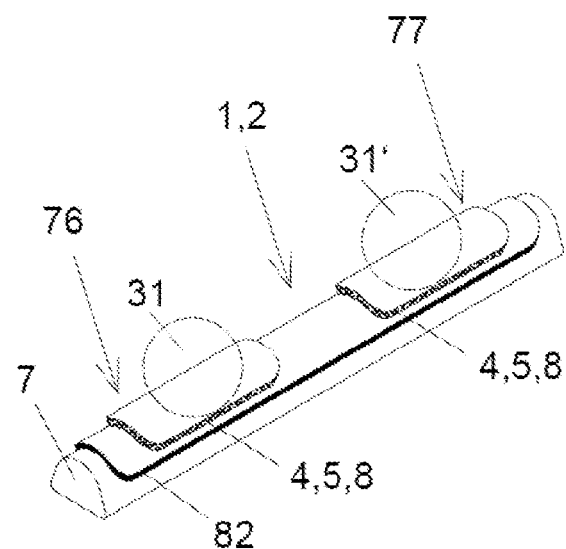
FIG. 21 shows an alternative preferred embodiment of a sensor half element and its cross-section with a partial insulating layer and two carrier material layer regions which contain the sensor compound.

As a consequence, the active surface is present in the junction area 31 only. Such sensor half element is shown in FIG. 21 and can be produced by e.g. printing. This figure also demonstrates that an insulating coating 82 is only required in and around the position of the desired junction area 31, which is high-lighted in FIG. 7. One alternative to the spatial resolved modification of sensor half elements 1, 2 is to coat and immobilize the sensor half elements 1, 2 homogenously. Afterwards the layers at regions outside the junction areas 31 are stripped. Light can be used to trigger a release reaction outside the shielded junction areas 31 when using photolabile linker to immobilize the sensor compounds 4, 5.

Example: Signal Enhancements Through Labeling

Dielectric macromolecules like DNA can be directed into the gap region 31 through non-uniform electric fields, a process which is called dielectrophoresis [Bakewell, 2006]. It increases the local concentrations of the analyte in the sensor array junctions and accelerates the molecular recognition events.

Signal enhancements can be enhanced through post labeling with materials which show strong interaction with alternating electric fields like conjugated polymers, metallic nanoparticles or other dielectrics.

Example: Increasing the Signal-to-Noise Ratio

In addition to the standard weave, which is made of regular warp and weft pattern, structures can be formed in which pairs of sensor half elements 1, 2 cross each other several times.

Alternatively, it is also possible that several electrodes can carry the same sensor compound 4, 5. Both methods lead to a build-in redundancy implying that multiple individual sensors are chemically and functional identical. By these means, the signal to noise ratio can be increased at the cost of the total integration density. Such a trade-off may become important for the measurements of rare analytes with small detectable total numbers which noticeably underlie the Poisson distribution. The built in parallel measurements decrease the confidence interval. For example, an average of 1000 molecules will mostly be detected at 1000±1 molecules and rarely outside the boundary of very few per mill. In contrast, a single molecule will show in approximately $\frac{1}{3}^{rd}$ of the measurement one, zero or two molecules, and rarely more than two. It corresponds to variations of ±100 percent. Only more than 3 measurements can pinpoint the correct result of 1 molecule and the confidence will increase with the number of measurements.

Of course, those ratios are considered for the whole measurement process from the sample preparation up to its measurement, but also in the design of the sensor array 12.

Example: Chaotic Fiber Matrix

Figure 22:
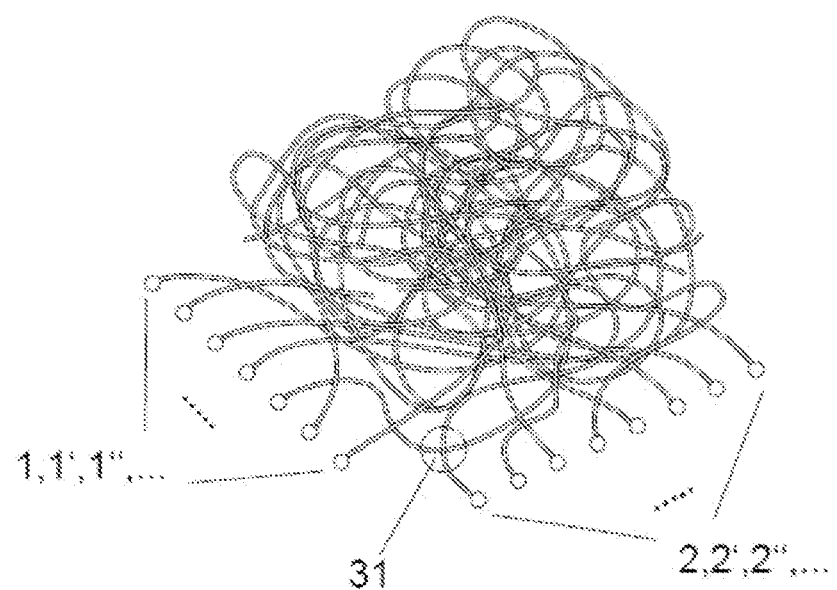
FIG. 22 shows a sensor array made from an unordered feltlike assembly of the sensor half elements.

Another embodiment of the invention further comprises sensor half elements 1, 2 which are combined in a nonwoven or feltlike structure as shown in FIG. 22, so that each sensor half element forms at least one junction with another sensor half element 1, 2. The sensor half elements 1, 2 are preferably round, flexible and elongated.

The sensor half elements 1, 2 are functionalized with sensor compounds. Formally, each of the sensor half elements 1, 2 can be defined as row element 1 or column element 2, if for example the row elements are functionalized with polynucleotide start site 911 specific sensor compounds and the column elements with end site 912 specific sensor compounds respectively.

The sensor half elements 1, 2 are not aligned in an ordered structure. If capacitance measurements are used as the readout method, the actual geometrical arrangement of the sensor half elements 1, 2 is irrelevant. The only requirement to determine the quantity of a certain kind of target molecule 9 is that there is a contact between the respective row element 1 and column element 2. It is possible that the wires can be arranged in a completely random way, provided that each two of them or each relevant pair faces each other at least once.

The geometrical arrangement of the sensor half elements 1, 2 is not defined. In FIG. 22 are only single ends of the sensor half elements 1, 2 attached to the sensor cell 150 and electrically contacted to the readout electronics. The sensor half elements 1, 2 are so long and arranged so chaotically, that the probability, that a sensor 3 is formed for each combination of row elements 1 and column elements 2, is sufficiently high for each combination.

In order to maintain equal chances for all row elements 1, 2 to form sensors 3 with each of the column elements 1, 2, it is advantageous to arrange the sensor half elements in a symmetrical way, e.g., around a ring or square for example.

In order to produce such sensor array, the sensor half elements 1, 2 are attached and electrically connected to measurement cell base, which can be a PCB used as land grid array. Second, the sensor half elements 1, 2 are agitated using chaotic air flow, mechanical shuttling, electrostatic force or similar methods in order to get chaotic rearrangement and mutual mixing of the sensor half elements 1, 2.

Third, the existing chaotic arrangement is fixed into a nearly planar structure by pressing the sensor half elements towards a common carrier. To ensure reliable contacts between the sensor half elements 1, 2 it is desired to exert moderate pressure on the sensor array permanently during the manufacturing process.

As a consequence, the randomness of the obtained structure implies that for each combination of sensor half elements 1, 2 under circumstances a different number of sensors 3 is formed. By measuring the impedance between the primary ports of the selection units 111, 112, which address the respective sensor half elements 1, 2, the number and size of sensors 3 can be measured. The upfront reference measurement is used for correcting the effects of different sizes and numbers of junction areas 31.

In analogy, the electrical reference measurement can be applied to every other sensor array according to the invention for eliminating the effects of different sizes of junction areas 31.

Sensor Half Elements with Optical Fibers and Scanning of Such Sensor Array

In the following, sensor arrays 12 according to the first preferred embodiment of the invention are provided, the sensor half elements 12 of which have a carrier 7 which is made from optical fibers, e.g. made of glass or transparent polymers.

Instead of the electrical measurements between the electrically conducting carriers 7, 74 of the sensor half elements 1, 2 an optical measurement of the light transition within the junction area 31 is utilized. The sensor compounds 4, 5 are immobilized onto transparent fibers, e.g. to glass via silane based interfacial binding layers from 3-aminopropyltrimethoxysilane or N-2-aminoethyl-3-aminopropyl-trimethoxy-silane, and the covalent binding to their exposed functional amino groups.

The sensor array network 12 is made either through weaving which results in a structure as shown in FIG. 1. Straight glass fibers can also be aligned in a frame which fixes the sensor half elements 1, 2 at the ends. A section of such kind of structure is shown in FIG. 8. The sensor arrays 12 are enclosed into a measurement cell 150 or cartridge which contains the microfluidic connections as well as the optical connections.

Local changes at junction areas 31 are measured by sending light from a laser, lamp or LED array through the blunt ends of one of the row elements 1 addressing or selecting one of row elements 1. Total internal reflection transmits or guides the light along the carrier 7 of row element 1. Bound sensor compounds 4, 5 in combination with the reacted analytes 9 modify the refractive index of the junction areas 31, which enables photons pass to the column element 2 of the respective junction area 31. Parts of the light crossing the junction area 31 enter the opposite column element and can be measured by photosensors which are connected to the column elements 2. Photosensors like photodiodes, -multiplier, -transistors or charge coupled devices CCD are arranged at one end of the column elements and receive and evaluate the optical signal. The optical signal can be transferred to a certain concentration or amount of substance within the sensor 3. The signal intensity at the individual sensors 3 corresponds to the amount of analyte which has been detected by the particular combination of sensor compounds 4, 5.

In contrast to electrical measurement, by means of optical measurement, all sensors 3 of one row element 1 can be measured at the same time.

Combinations with fluorescent labeling methods are within the range of visible light which helps to increase the sensitivity of such assays.

Figure 23:
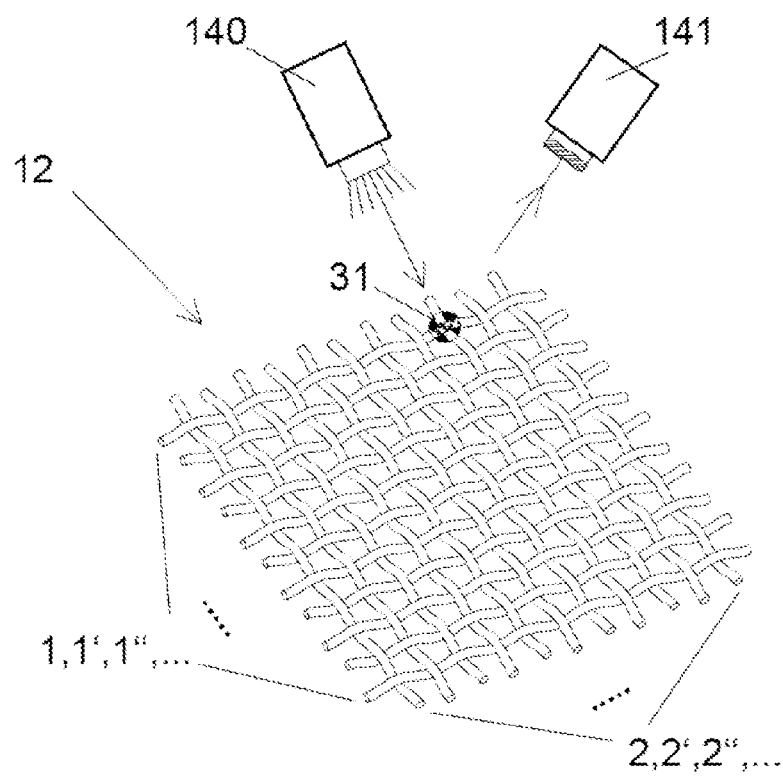
FIG. 23 shows one measurement method for determining the concentration of the segregated analyte with a light source and a light detector unit.

Example: Preparation of Transparent Sensor Half Elements for Peripheral Optical Read-Out Another embodiment of the invention, shown in FIG. 23, comprises carriers 7 made from optical fibers, e.g. made of glass or transparent polymers, each of which is functionalized with the sensor compounds 4, 5. The sensor compounds are immobilized onto the surface of the sensor half elements 1, 2 or enclosed into a polymer network, the carrier 7 or into the material layer 83. The sensor array network 12 is formed by weaving (FIG. 1) or the straight alignment of sensor half elements (FIG. 8) into a frame and enclosed into a cartridge or sensor cell 150 containing microfluidic connections. No contacts of the fibers to light source and photosensor are required.

The processing of the sample occurs inside the cartridge or sensor cell 150 which involves washing and preconditioning steps, filling with the analyte, adding of enzyme and additives like fluorophors for performing e.g. PCR together with labeling, and finally washing steps to reduce the background signal level.

The sensor cell 150 is opened to remove the processed sensor array 12, which is transferred to a standard micro array scanner. The signal intensity at the individual sensors 3 corresponds to the amount of analyte which has been detected by the particular sensor compound combination 4, 5.

The micro array scanner comprises at least one optical radiation source 140 directed towards the junction areas 31 of the sensor array 12. One optical radiation detecting unit 141 is directed towards the junction areas 31 of the sensor array 12. The optical radiation detecting unit 141 measures radiation absorbed and/or re-emitted by the organic compounds 9 under investigation being bound to the sensor compounds 4, 5 in the respective junction area 31.

Experimental Results
Experimental Confirmation Part I

This example describes use of a sensor array 12 made from blank insulated sensor half elements 1, 2 to determine spatially resolved concentrations changes of analyte in solution through impedance measurements at single frequency. The experiment illustrates the working principle to distinguish compounds in solution with junction resolution using a self supporting conductor array 12.

Measurement Device

A 4×4 net junction sensor array 12 of 16 sensor fields 31 in total has been built using 50 μm copper wires 74 with a 5 μm PU coating 82. The wires had been woven to a self-supporting structure which was held in a frame on a glass support. Connections were made through soldering. The potentiostat and frequency analyzer was a REF 600 system from Gamry, Inc. USA.

Impedimetric Measurement

Impedance scans were made across a wide frequency range to characterize each junction, starting at 1 MHz and stepping down at logarithmic scale with 10 points per decade to 1 KHz. Typical impedance spectra are shown in FIG. 12. At a phase shift of −90° is only the capacitance visible as active element. A simple fitting algorithm reveals the value for the capacitances. Single junction measurements are used to record calibration curves which relate different concentrations to capacitance values as shown for PEG300/water mixtures in FIG. 13. Accuracy of the repeated capacitance measurement is ±0.8%.

For well characterized sensor array systems is it not further necessary to record complex impedance spectra because those measurements are time consuming in particular at lower frequencies. If the characteristic of the system does not change, it is sufficient to measure the modulus or phase only.

Single frequency measurements have been carried in this experiment out at 100 KHz and the effective potential, $U_{eff}$, of 707 mV. The peak potentials, $U_{max}$, are ±1V, potentials which enable electrochemical reactions at electrode surfaces. The insulting layer hinders the electron transfer. Only the electrical field transmits through the junction. The insulating layer is with 5 μm relative thick. The assumption has been made, that at this frequency the largest contribution to the overall resistivity results from the capacitive coupling across the gap junction.

First, reference values are taken for background correction. Filled with ultra-filtered water, all 16 junctions, denoted as $a_{i,j}$, were measured at the open circuit potential, $E_{OC}$, $U_{eff}$ of 707 mV and low noise setting. By this means $Z_{mod}$ could be recorded as reference value for each junction. Second, one modification has been inserted manually into the dry cell at junction $a_{2,2}$. For this purpose silicon grease from Corning, N.Y., USA has been manipulated using a sharp tip. Afterwards, the cell has been washed several times with ultrafiltered-water before filling. The very same measurement routine has been applied again.

Tab. 1 contains all background corrected $Z_{mod}$ values. A tilt of the baseline has been compensated through a correction. The reading at the modified junction has been 0.23 MO above the surrounding non-modified junctions

TABLE 1

| | A | | | | | B | | | |
|---|---|---|---|---|---|---|---|---|---|
| | 1 | 2 | 3 | 4 | | 1 | 2 | 3 | 4 |
| 1 | 0.30 | 0.29 | 0.26 | 0.31 | 1 | 0.04 | 0.02 | −0.03 | 0.01 |
| 2 | 0.30 | 0.58 | 0.32 | 0.41 | 2 | −0.02 | 0.23 | −0.06 | 0.00 |
| 3 | 0.33 | 0.40 | 0.42 | 0.53 | 3 | −0.05 | −0.02 | −0.05 | 0.02 |
| 4 | 0.40 | 0.49 | 0.53 | 0.59 | 4 | −0.04 | −0.01 | −0.03 | −0.03 |

Table 1 presents the modulus of measured capacitances $Z_{mod}$ in MΩ recorded at $10^5$ Hz and $U_{eff}$±707 mV in a 4×4 50 μm copper 5 μm PU coated wire net junction cell. The measurement of Table A was taken in water after a modification of junction $a_{2,2}$ with silicon grease minus reference measurement. The result of table B is corrected via a smooth tilt according to f(R)=R−a−i·b−i·j·c, a=0.2 MΩ, b=0.045 MΩ and c=0.015 MΩ. The modified junction is emphasized.

The impedance magnitude of the modified junction $a_{2,2}$ is larger which means that the capacitance and therefore the dielectric in the junction is smaller. Water has an $\in_r$ of 80, whereas the silicon grease has a value below 10.

Experimental Confirmation Part II

The experiment demonstrates the principle of detecting dielectric variations in solution with spatial resolution using a self supporting electrode array. The analyte is DNA.

The Device

A 24×24 net junction sensor array 12 has been built using 50 μm copper wires with a 5 μm PU coating. The wires have been woven to a self-supporting structure using a purpose build loom, and held in a circuit board frame. The cell has been completed by a glass base and opens to the upside. Connections were made through soldered leads to a purpose built circuit switch board which contained 2×24 selection units 111, 112 formed by transistor switches together with other supporting electronic devices. The switches are able to set each electrode to signal line or alternatively to floating ground. The selection units 111, 112 is controlled by a software program via a USB port. The software controls also the HP 4285A LCR meter measurement instrument 130.

Results

Figure 24:
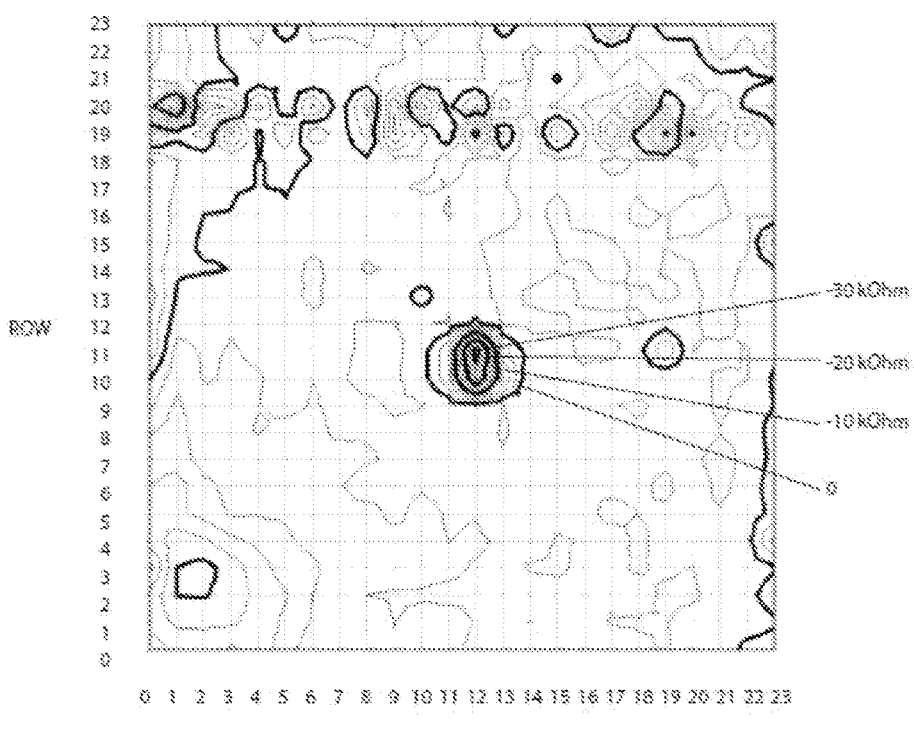
FIG. 24 shows the contour plot of the differential impedance modulus scan using a 24×24 sensor array where one drop of diluted DNA solution has been inserted into water in central position.

FIG. 24 shows the differential modulus of the impedance scan at 1 MHz in the sensor array 12. Scanning refers to the sampling of all consecutive sensor junctions or junction areas starting from $a_{0,0}$, row 0 and column 0, to $a_{23,23}$, which has been addressed through the $23^{rd}$ sensor half elements. First, a reference scan has been taken with the sensor field entirely submerged in ultrafiltrated water. Second, 1 μl of saturated fish sperm DNA, has been injected into the central position of the sensor array 12. The difference of the modulus shows a decrease at the position of the injection in the first scan immediately after injection which has disappeared in the scan following 2.5 min later. A decrease in the modulus occurs due to an increase of the capacitance through the increase of the dielectric in the gap region [Takashima, 1984].

Due to the relative thick coating of 5 μm is also the closest distance between the electrodes with 10 μm large and the sensor's active gap region very small in comparison. The surface carries no functionalization yet and therefore is the amount of DNA which enters the gap region small and does not become accumulated through molecular recognition. Only a diluted part of the injected sample becomes detectable. Foremost, the experiment demonstrates the principle of electrical detection of local DNA concentration differences at junction of insulated sensor half elements 1, 2.

REFERENCES CITED

Patent Publications

Albers J. et al. (1999) Electric Sensor Array. WO 0062047 A1, Fraunhofer Gesellschaft.
Boles T. C., Abrams E. S. (2002) Solid phase methods for amplifying multiple nucleic acids. WO 0075374 A1, Mosaic technologies.
Connolly D. M. et al. (2002) High resolution DNA detection methods and devices. US 2002/0022223 A1, Integrated Nano-Technologies.
Connolly D. M. et al. (2006) Detection card for analyzing a sample for a target nucleic acid molecule, and uses therefore. US 2006/0019273 A1, Integrated Nano-Technologies.
Frey A. et al. (2004) Biosensor array and method for operating a biosensor array, WO 2004/001405 A1, Infineon.
Gao Z, Chen X. (2010) Electrical Sensor for ultrasensitive nucleic acid detection. WO 2010/104479 A1, Agency for Science, Technology and Research
Lee J. W., Thundat T. G. (2005) DNA and RNA sequencing by nanoscale reading through programmable electrophoresis and nanoelectrode-gated tunneling and dielectric detection. U.S. Pat. No. 6,905,586 B2, Inventors.
Lee L. (2005) Method and apparatus for nanogap device and array. WO 2005/008540, University of California.
Li C. (2005) Addressable Chem-Bio Chip Array. WO 2005095991 A1, Nanyan TU.
Liu Z. Z. (2007) Microelectrode biosensing chip of 3D nanogap mesh array. CN 101046458, Institute of Electronics.
Maeda H. et al. (2004) Sensor cell, bio-sensor, capacitance element manufacturing method, biological reaction detection method and genetic analytical method. US2004110277 A1, SEIKO EPSON CORP.
Maracas G. (2000) Column and Row Addressable High Density Biochip Array. CA 2393766 A1, Motorola.
Scuor N. (2007) Method and System for Generating Pattern Recognition. WO2007068719 A1, Uni Trieste.
Seitz A. (2007) Polynucleotide amplification, WO2007062445 A1, Inventor
Steinmüller-Nethl D. et al. (2009) Methode for identifying and quantifying organic and biochemical substances. WO 2009/003208 A1, ARC Austrian Research Centers.
Southern E. (1997) Apparatus and method for analyzing polynucleotide sequences and method of generating oligonucleotide arrays. U.S. Pat. No. 5,700,637 A, ISIS Innovation.

Other Publications

Adessi C., Matton G., Ayala G., Turcatti G., Mermod J.-J., Mayer P., Kawashima E. (2000) Solid phase DNA amplification: characterisation of primer attachment and amplification mechanisms Nucl. Acids Res. 28 (20) e87.
Bakewell D. J., Morgan H. (2006) Dielectrophoresis of DNA: Time- and frequency-dependent collections on microelectrodes. IEEE Transactions on Nanobioscience 5:1-8.
Berdat D., Marin A., Herrera F., Gijs M. A. M. (2006) DNA biosensor using fluorescence microscopy and impedance spectroscopy. Sensors and Actuators B: Chemical 118(1-2):53-9.
Braun E., Eichen Y., Sivan U., Ben-Yoseph G. (1998) DNA-templated assembly and electrode attachment of a conducting silver wire. Nature 391, 775-8.
Brewood G. P., Rangineni Y., Fish D. J., Bhandiwad A. S., Evans D. R., Solanki R., Benight A. S. (2008) Electrical detection of the temperature induced melting transition of a DNA hairpin covalently attached to gold interdigitated microelectrodes. Nucleic Acids Res. 36(15):e98.
Cal H., Zhu N., Jiang Y., He P., Fang Y. (2003) Cu@Au alloy nanoparticle as oligonucleotides labels for electrochemical stripping detection of DNA hybridization. Biosens Bioelectron. 18(11):1311-9.
Carminati M., Ferrari G., Sampietro M. (2009) Attofarad resolution potentiostat for electrochemical measurements on nanoscale biomolecular interfacial systems. Rev. Sci. Instrum. 80(12), 124701.
Chen J. C., McGaughy B. W., Sylvester D., Hu C. (1996) An On-chip Attofarad Interconnect Charge-based Capacitance Measurement (CBCM) technique, IEDM Tech. Dig., pp. 3.4.1-3.4.4.
Cho M., Le S., Han S. Y., Park J. Y., Rahman M. A., Shim Y. B., Ban C. (2006) Electrochemical detection of mismatched DNA using a MutS probe. Nucleic Acids Res. 34(10):e75.
Dharuman V., Grunwald T., Nebling E., Albers J., Blohm L., Hintsche R. (2005) Label-free impedance detection of oligonucleotide hybridisation on interdigitated ultramicroelectrodes using electrochemical redox probes. Biosens Bioelectron. 21(4):645-54.
Drummond T. G., Hill M. G., Barton J. K. (2003) Electrochemical DNA sensors. Nat. Biotechnol. 21(10):1192-9.
Fojta M., Havran L., Billova S., Kostecka P., Masarik M., Kizek R. (2003) Two-Surface Strategy in Electrochemical DNA Hybridization Assays: Detection of Osmium-Labeled Target DNA at Carbon Electrodes. Electroanalysis 15(5): 431-40.
Gheorghe M., Guiseppi-Elie A. (2003) Electrical frequency dependent characterization of DNA hybridization. Biosens Bioelectron. 19(2):95-102.
Hang T. C., Guiseppi-Elie A., (2004) Frequency dependent and surface characterization of DNA immobilization and hybridization. Biosensors and Bioelectronics 19(11): 1537-48.
Hashimoto K., Ito K., Ishimori Y. (1994) Sequence-specific gene detection with a gold electrode modified with DNA probes and an electrochemically active dye. Anal Chem. 66(21):3830-3.
Hasoň S., Dvořák J., Jelen F., Vetterl V. (2002) Interaction of DNA with echinomycin at the mercury electrode surface as detected by impedance and chronopotentiometric measurements. Talanta 56(5):905-13.
Henning A., Henkel J., Bier F. F., Hölzel R. (2008) Label-free electrical quantification of the dielectrophoretic response of DNA. PMC Biophys. 1(1):4.
Horn T., Urdea M. S. (1989) Forks and combs and DNA: the synthesis of branched oligodeoxyribonucleotides. Nucleic Acid Res 17:6959-67.

Hwang J. S., Kong K. J., Ahn D., Lee G. S., Ahn D. J., and Hwang S. W. (2002) Electrical transport through 60 base pairs of poly(dG)-poly(dC) DNA molecules. Appl. Phys. Lett. 81, 1134.

Iqbal S. M., Balasundaram G., Subhasis Ghosh, Bergstrom D. E., Bashir R. (2005) Direct current electrical characterization of ds-DNA in nanogap junctions. Appl. Phys. Lett. 86(15):153901.

Kelley S. O., Boon E. M., Barton J. K., Jackson N. M., Hill M. G. (1999) Single-base mismatch detection based on charge transduction through DNA. Nucleic Acids Res. 27(24):4830-7.

Lasia A. (1999) Electrochemical Impedance Spectroscopy and its Application. Modern Aspects of Electrochemistry 32:143-248.

Laureyn W., Nelis D., Van Gerwen P., Baert K., Hermans L., Magnee R., Pireaux J.-J., Maes G. (2000) Nanoscaled interdigitated titanium electrodes for impedimetric biosensing. Sensors and Actuators B: Chemical 68(1-3):360-370.

Li A., Yang F., Ma Y., Yang X. (2007) Electrochemical impedance detection of DNA hybridization based on dendrimer modified electrode. Biosensors and Bioelectronics 22(8): 1716-22.

Li C. Z., Long Y. T., Lee J. S., Kraatz H. B. (2004) Protein-DNA interaction: impedance study of MutS binding to a DNA mismatch. Chem Commun (Camb). 5:574-5.

Li C. Z., Liu Y., Luong J. H. (2005) Impedance sensing of DNA binding drugs using gold substrates modified with gold nanoparticles. Anal Chem. 77(2):478-85.

Lillis B., Manning M., Hurley E., Berney H., Duane R., Mathewson A., Sheehan M. M. (2007) Investigation into the effect that probe immobilisation method type has on the analytical signal of an EIS DNA biosensor. Biosensors and Bioelectronics 22(7):1289-95.

Lisdat F., Schäfer D. (2008) The use of electrochemical impedance spectroscopy for biosensing. Anal Bioanal Chem. 391 (5):1555-67.

Lu J-Q., Zhang X-G. (2008) Nucleotide capacitance calculation for DNA sequencing. Biophys J. 95(9):L60-2.

Ma K.-S., Zhou H., Zoval J., Madou M. (2006) DNA hybridization detection by label free versus impedance amplifying label with impedance spectroscopy. Sensors and Actuators B: Chemical 114(1):58-64.

Maupas H., Soldatkin A. P., Martelet C., Jaffrezic-Renault N., Mandrand B. (1997) Direct immunosensing using differential electrochemical measurements of impedimetric variations Journal of Electroanalytical Chemistry 421 (1-2):165-71.

Mercier J.-F., Slater G. W. (2003) Solid Phase DNA Amplification: A Brownian Dynamics Study of Crowding Effects. Biophysical Journal 89 (1) 32-42.

Montelius L., Tegenfeldt J. O., Ling T. G. I. (1995) Fabrication and characterization of a nanosensor for admittance spectroscopy of biomolecules. J. Vac. Sci. Technol. A13 (3):1755-60.

Pänke O., Kirbs A., Lisdat F. (2007) Voltammetric detection of single base-pair mismatches and quantification of label-free target ssDNA using a competitive binding assay. Biosens Bioelectron. 22(11):2656-62.

Pänke O., Balkenhohl T., Kafka J., Schäfer D., Lisdat F. (2008) Impedance spectroscopy and biosensing. Adv Biochem Eng Biotechnol. 109:195-237.

Patolsky F., Lichtenstein A., Willner I. (2001) Electronic transduction of DNA sensing processes on surfaces: amplification of DNA detection and analysis of single-base mismatches by tagged liposomes. J Am Chem. Soc. 123(22):5194-205.

Patolsky F, Lichtenstein A, Willner I. (2003) Highly sensitive amplified electronic detection of DNA by biocatalyzed precipitation of an insoluble product onto electrodes. Chemistry 9(5):1137-45.

Peng H., Soeller C., Cannell M. B., Bowmaker G. A., Cooney R. P., Travas-Sejdic J. (2006) Electrochemical detection of DNA hybridization amplified by nanoparticles. Biosens Bioelectron. 21(9):1727-36.

Pohl H. A. (1986) Giant polarization in high polymers. Journal of Electronic Materials 15:201.

Reed M. A., Zhou C., Muller C. J., Burgin T. P., Tour J. M. (1997) Conductance of a Molecular Junction. Science 278(5336):252-254.

Reichert J., Ochs R., Beckmann D., Weber H. B., Löhneysen H. v. (2002) Driving current through single organic molecules. Physical Review Letters 88:176804.

Schlecht U., Malave A., Gronewold T., Tewes M., Lohndorf M. (2006) Comparison of antibody and aptamer receptors for the specific detection of thrombin with a nanometer gap-sized impedance biosensor. Anal Chim Acta 573-574: 65-8.

Sigalov G., Comer J., Timp G., Aksimentiev A. (2008) Detection of DNA sequences using an alternating electric field in a nanopore capacitor. Nano Lett. 8 (1):56-63.

Strasák L., Dvorák J., Hason S., Vetterl V. (2002) Electrochemical impedance spectroscopy of polynucleotide adsorption. Bioelectrochemistry 56(1-2):37-41.

Takashima S., Gabriel C., Sheppar R. J., Grant E. H. (1984) Dielectric behavior of DNA solution at radio and microwave frequencies (at 20 degrees C.). Biophys J. 46(1): 29-34.

Van Gerwen P., Laureyn W., Laureys W., Huyberechts G., Op De Beeck M., Baert K., Suls J., Sansen W., Jacobs P., Hermans L., Mertens R. (1998) Nanoscaled interdigitated electrode arrays for biochemical sensors. Sensors and Actuators B: Chemical 49(1-2):73-80.

Vermeeren V., Bijnens N., Wenmackers S., Daenen M., Haenen K., Williams O. A., Ameloot M., Vandeven M., Wagner P., Michiels L. (2007) Towards a real-time, label-free, diamond-based DNA sensor. Langmuir 23 (26): 13193-202.

Xu Y., Yang L., Ye X., He P., Fang Y. (2006) Impedance-Based DNA Biosensor Employing Molecular Beacon DNA as Probe and Thionine as Charge Neutralizer. Electroanalysis 18(9):873-81.

Yan F., Sadik O. A. (2001) Enzyme-modulated cleavage of dsDNA for studying interfacial biomolecular interactions. J Am Chem. Soc. 123(46):11335-40.

Yi M., Jeong K.-H., Lee L. P. (2005) Theoretical and experimental study towards a nanogap dielectric biosensor. Biosens Bioelectron. 20 (7):1320-6.

Yoo J. S., Park S. M. (2000) An electrochemical impedance measurement technique employing Fourier transform. Anal Chem. 72 (9):2035-41.

Zielke U., Hüttinger K. J. and Hoffman W. P. (1996) Surface-oxidized carbon fibers: I. Surface structure and chemistry. Carbon 34(8):983-98.

The invention claimed is:
1. A sensor array, comprising:
a) a plurality of sensor half elements for measuring a concentration and identifying a plurality of organic target compounds under investigation or related copies thereof within a mixture of organic compounds at least one of said sensor half elements or all of said sensor half elements including an electrical conductor forming a carrier, an electrically insulating layer completely encasing said electrical conductor and a layer of a sensor compound supported on said carrier and said insulating layer;
b) said layer of sensor compound including a plurality of different sensor compounds wherein each sensor half element contains and/or carries one of said sensor compounds, the sensor compounds binding to a specific binding site of said target compounds, respectively;
c) wherein each of said sensor compounds is assigned to at least one of said sensor half elements;
d) wherein each sensor half element intersects or traverses at least one of the other said sensor half elements in a separate junction area;
e) wherein said sensor compounds of two intersecting or traversing sensor half elements are spaced and/or converge and/or touch each other;
f) wherein in each junction area an individual sensor is formed with a determined combination of two sensor compounds each said sensor compound being located at one of the intersecting or traversing sensor half elements; and
g) the sensor array having at least two junction areas with different combinations of sensor compounds;
h) said sensor half elements being aligned in a grid structure, with a plurality of row elements and a plurality of column elements;
i) said row elements being formed by a number of sensor half elements and said column elements being formed by the remaining said sensor half elements;
j) said row elements being aligned and spaced next to each other and said column elements being aligned and spaced next to each other;
k) each said row element intersecting each said column element in at least one said junction area; and
l) each said junction area forming an individual sensor.

2. The sensor array according to claim 1, wherein a number of said row elements equals a number of said column elements.

3. The sensor array according to claim 1, wherein:
said carrier is selected from the group consisting of a filament, a string, a wire, a conductor, a band and a fiber, and said carrier supports a layer of the respective sensor compound or includes the respective said sensor compound; and/or
at least one of said sensor half elements or all of said sensor half elements contain a surface-bound carrier material layer containing said sensor compound.

4. The sensor array according to claim 1, further comprising a common carrier and wherein at least one of the following is true:
a plurality of said sensor half elements are disposed on said common carrier; or
said common carrier comprises said plurality of sensor half elements; or
a number of said sensor half elements are formed as part of said common carrier; or
said common carrier is plate-shaped.

5. The sensor array according to claim 4, wherein said common carrier is made of a material or contains a material or supports a material layer, with said material or said material layer containing said sensor compound of the respective said sensor half element in mutually separated areas.

6. The sensor array according to claim 1, further comprising:
a first common carrier and a second common carrier;
said row elements are disposed on said first common carrier or are formed as part of said first common carrier; and
said column elements are disposed on said second common carrier or are formed as part of said second common carrier.

7. The sensor array according to claim 6, wherein one or both of said first common carrier or said second common carrier have a shape of a plate.

8. The sensor array according to claim 7, wherein:
one or both of said first and second common carriers are made of material or contain material or support a material layer;
said material or said material layer containing said sensor compound of the respective said sensor half element in mutually separated areas.

9. The sensor array according to claim 1, wherein the respective said sensor compound is disposed exclusively in said junction areas, or the respective said sensor compound covers at least a part or a complete surface of said sensor half elements.

10. The sensor array according to claim 3, wherein said carrier is selected from the group consisting of an electrical conductor, an optical conductor, and a wave guide, and said conductors or wave guides are made from metal, glass fiber or conducting polymer.

11. The sensor array according to claim 3, wherein at least one of the following is true:
said carrier contains an electrically insulating layer which partially or entirely surrounds an electrical conductor thereof; and/or
said sensor compound is located and/or immobilized at said insulating layer; and/or
said insulating layer contains a material in which said sensor compound is embedded; and/or
said sensor compound is contained in a carrier material layer; and/or
said sensor compound is contained in a gel or polymer arranged on said insulating layer and/or
encoating said insulating layer.

12. The sensor array according to claim 1, wherein at least one of the following is true:
at least a portion of a circumference of a cross-section of said sensor half elements is convex;
said cross section is approximately circular or elliptic;
a gap of said junction area between said sensor half elements is at least partially cuneiform and/or slit shaped and/or said gap includes a narrowing region;
said sensor half elements contain a structured and/or wavy and/or porous and/or rough surface;
said sensor half elements are arranged on elevations or in cavities of a first common carrier and/or of a second common carrier.

13. The sensor array according to claim 1, wherein:
said sensor half elements are aligned in a woven structure; or
said sensor half elements are combined in a feltlike or unordered structure, so that each said sensor half element forms at least one junction with another said sensor half element.

14. The sensor array according to claim 1, wherein:
said sensor half elements are straight and contact each other in the respective said junction area; or said sensor half elements are curved and contact each other in the respective said junction area.

15. The sensor array according to claim 14, wherein:
if said sensor half elements are straight, said junction area therebetween is a substantially punctiform region; and
if said sensor half elements are curved, said junction area therebetween is a unidimensional line or two dimensional region.

16. The sensor array according to claim 1, wherein:
said row elements are aligned in a first plane and said column elements are aligned in a second plane;
said row and column elements are narrowed to each other in said junction areas or touch each other or junction areas converge;
and/or
a first common carrier and a second common carrier are planar plates or frames, and said common carriers are contacted so that said row elements approach or contact column elements within a junction area, and said sensor compounds of said sensor half elements approach each other in junction areas.

17. The sensor array according to claim 1, wherein:
within said junction areas molecules of said sensor compound of said row sensor elements and molecules of said sensor compound of said column sensor elements are spaced so that organic compounds under investigation or related copies thereof are able to bind to the respective said sensor compound arranged on said row elements with a first binding site and to the respective said sensor compound arranged on said column elements with a second binding site;
the respective said sensor compounds of said sensor half elements contain oligonucleotides, binding to said binding sites of the target compounds or organic polymers or DNA or RNA molecules; and/or
the respective said sensor compounds of said row elements bind to start sites of organic polymers or DNA or RNA molecules and the respective said sensor compounds of said column elements bind to end sites of an organic polymer or DNA or RNA molecules.

18. The sensor assembly, comprising:
a sensor array according to claim 1; and
an evaluation unit having:
  a first selection unit with one primary port and a plurality of secondary ports individually connected to one sensor half element each;
  a second selection unit with one primary port and a plurality of secondary ports individually connected to one sensor half element each;
  a control unit configured to control said selection units to address and/or select a first sensor half element with said first selection unit and a second sensor half element with said second selection unit; and
  a measurement unit connected to said primary ports of said primary and secondary selection units and configured for recording electrical, electromagnetic or optical parameters.

19. The sensor assembly according to claim 18, wherein:
said measurement unit is an impedance, electromagnetic wave impedance, capacitance, light absorption detection unit; and
said row elements are individually connected to said secondary ports of said first selection unit and the column elements are individually connected to said secondary ports of said second selection unit.

* * * * *